US009554783B2

(12) United States Patent
Pavcnik et al.

(10) Patent No.: US 9,554,783 B2
(45) Date of Patent: Jan. 31, 2017

(54) CLOSURE DEVICE AND METHOD OF CLOSING A BODILY OPENING

(75) Inventors: Dusan Pavcnik, Portland, OR (US); Kurt J. Tekulve, Ellettsville, IN (US)

(73) Assignees: COOK MEDICAL TECHNOLOGIES LLC, Bloomington, IN (US); OREGON HEALTH AND SCIENCE UNIVERSITY, Portland, OR (US)

( * ) Notice: Subject to any disclaimer, the term of this patent is extended or adjusted under 35 U.S.C. 154(b) by 2051 days.

(21) Appl. No.: 12/533,731

(22) Filed: Jul. 31, 2009

(65) Prior Publication Data

US 2010/0030259 A1    Feb. 4, 2010

Related U.S. Application Data

(63) Continuation of application No. PCT/US2008/001422, filed on Feb. 1, 2008.
(Continued)

(51) Int. Cl.
*A61B 17/08* (2006.01)
*A61B 17/00* (2006.01)

(52) U.S. Cl.
CPC .... *A61B 17/0057* (2013.01); *A61B 2017/0061* (2013.01); *A61B 2017/00243* (2013.01);
(Continued)

(58) Field of Classification Search
CPC ................. A61B 17/0057; A61B 2017/00575; A61B 2017/00592; A61B 2017/00597; A61B 2017/0061; A61B 2017/00615
(Continued)

(56) References Cited

U.S. PATENT DOCUMENTS 3,012,882 A    12/1961  Muldawer et al. ............. 75/170
3,174,851 A     3/1965  Buechler et al. .............. 75/170
(Continued)

FOREIGN PATENT DOCUMENTS

EP    1 281 355 A2    2/2003
EP    1 281 355 A3    2/2003
(Continued)

OTHER PUBLICATIONS

ISR/Written Opinion of PCT/US2008/001422, dated Aug. 4, 2009, (14p).
(Continued)

*Primary Examiner* — Robert Lynch
(74) *Attorney, Agent, or Firm* — Brinks Gilson & Lione

(57) ABSTRACT

In one embodiment, a device for closing or occluding ASDs and PFOs, or other bodily passageways, includes a circumferential frame, a sheet of biocompatible material attached to the frame, and at least one anchor attached to the sheet of biocompatible material. In another embodiment, the closure device includes a circumferential frame, at least one crossbar extending across and attached to the frame, at least one anchor connected to at least one crossbar; and at least one sheet of biocompatible material (such as ECM material) attached to the frame. The anchor includes at least one grasping member having a structure, such as a wired loop, which is configured for releasable attachment to a delivery release member, which facilitates delivery of a closure device collapsibly disposed in a delivery catheter. Alternatively, one or more anchor end pairs may be connected to a delivery bar enhancing delivery and retrieval of the device.

17 Claims, 16 Drawing Sheets

Related U.S. Application Data

(60) Provisional application No. 60/898,834, filed on Feb. 1, 2007.

(52) U.S. Cl.
CPC ............... *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/00623* (2013.01)

(58) Field of Classification Search
USPC ................. 606/213.215, 139, 151, 153, 157, 213,606/215–217, 232; 128/898
See application file for complete search history.

(56) References Cited

U.S. PATENT DOCUMENTS

| | | | |
|---|---|---|---|
| 3,772,137 A | 11/1973 | Tolliver | 161/169 |
| 3,953,566 A | 4/1976 | Gore | |
| 4,665,906 A | 5/1987 | Jervis | 128/92 |
| 4,675,361 A | 6/1987 | Ward, Jr. | 525/92 |
| 4,836,204 A | 6/1989 | Landymore et al. | |
| 4,861,830 A | 8/1989 | Ward, Jr. | |
| 4,911,163 A | 3/1990 | Fina | |
| 4,917,089 A | 4/1990 | Sideris | 606/215 |
| 5,017,664 A | 5/1991 | Grasel et al. | |
| 5,020,612 A | 6/1991 | Williams | 175/234 |
| 5,024,671 A | 6/1991 | Tu et al. | |
| 5,108,420 A | 4/1992 | Marks | 606/213 |
| 5,167,628 A | 12/1992 | Boyles | |
| 5,176,692 A | 1/1993 | Wilk et al. | |
| 5,192,301 A | 3/1993 | Kamiya et al. | |
| 5,258,000 A | 11/1993 | Gianturco | 606/151 |
| 5,284,488 A | 2/1994 | Sideris | 606/21 |
| 5,334,217 A | 8/1994 | Das | 606/213 |
| 5,417,708 A | 5/1995 | Hall et al. | |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,486,195 A | 1/1996 | Myers et al. | |
| 5,589,563 A | 12/1996 | Ward et al. | |
| 5,595,571 A | 1/1997 | Jaffe et al. | 8/94.11 |
| 5,635,936 A | 6/1997 | Rybicki | |
| 5,643,317 A | 7/1997 | Pavcnik et al. | 606/213 |
| 5,669,933 A | 9/1997 | Simon et al. | |
| 5,683,411 A | 11/1997 | Kavteladze et al. | |
| 5,690,642 A | 11/1997 | Osborne et al. | 606/108 |
| 5,702,421 A | 12/1997 | Schneidt | |
| 5,709,707 A | 1/1998 | Lock | 606/213 |
| 5,720,777 A | 2/1998 | Jaffe et al. | 623/2 |
| 5,725,534 A | 3/1998 | Rasmussen | |
| 5,733,337 A | 3/1998 | Carr, Jr. et al. | |
| 5,769,796 A | 6/1998 | Palermo et al. | 600/585 |
| 5,772,632 A | 6/1998 | Forman | |
| 5,797,953 A | 8/1998 | Tekulve | |
| 5,797,960 A | 8/1998 | Stevens et al. | |
| 5,814,061 A | 9/1998 | Osborne et al. | 606/194 |
| 5,843,180 A | 12/1998 | Jaffe et al. | 623/2 |
| 5,843,181 A | 12/1998 | Jaffe et al. | 623/2 |
| 5,846,247 A | 12/1998 | Unsworth et al. | 606/108 |
| 5,846,261 A | 12/1998 | Kotula et al. | |
| 5,853,422 A | 12/1998 | Huebsch et al. | 606/213 |
| 5,861,003 A | 1/1999 | Latson et al. | |
| 5,879,366 A | 3/1999 | Shaw et al. | 606/213 |
| 5,944,738 A | 8/1999 | Amplatz et al. | |
| 5,947,997 A | 9/1999 | Pavcnik et al. | 606/213 |
| 5,960,642 A | 10/1999 | Kim et al. | |
| 5,980,799 A | 11/1999 | Martakos et al. | |
| 5,993,844 A | 11/1999 | Abraham et al. | 424/423 |
| 6,063,113 A | 5/2000 | Kavteladze et al. | |
| 6,077,281 A | 6/2000 | Das | 606/151 |
| 6,077,291 A | 6/2000 | Das | 606/213 |
| 6,080,182 A | 6/2000 | Shaw et al. | 606/213 |
| 6,113,623 A | 9/2000 | Sgro | 606/215 |
| 6,117,157 A | 9/2000 | Tekulve | |
| 6,117,159 A | 9/2000 | Huebsch et al. | 606/213 |
| 6,193,731 B1 | 2/2001 | Oppelt et al. | 606/151 |
| 6,206,907 B1 | 3/2001 | Marino et al. | 606/215 |
| 6,206,931 B1 | 3/2001 | Cook et al. | 623/23.75 |
| 6,214,029 B1 | 4/2001 | Thill et al. | |
| 6,238,416 B1 | 5/2001 | Sideris | |
| 6,296,657 B1 | 10/2001 | Brucker | |
| 6,342,064 B1* | 1/2002 | Koike et al. | 606/213 |
| 6,346,074 B1 | 2/2002 | Roth | |
| 6,355,052 B1 | 3/2002 | Neuss et al. | 606/213 |
| 6,358,228 B1 | 3/2002 | Tubman et al. | |
| 6,358,284 B1 | 3/2002 | Fearnot et al. | 623/23.72 |
| 6,368,338 B1 | 4/2002 | Konya et al. | |
| 6,371,961 B1 | 4/2002 | Osborne et al. | 606/108 |
| 6,379,368 B1 | 4/2002 | Corcoran et al. | 606/153 |
| 6,451,052 B1 | 9/2002 | Burmeister et al. | 623/1.16 |
| 6,458,137 B1 | 10/2002 | Klint | |
| 6,547,815 B2 | 4/2003 | Myers | |
| 6,572,650 B1 | 6/2003 | Abraham et al. | 623/1.38 |
| 6,623,508 B2 | 9/2003 | Shaw et al. | 606/213 |
| 6,656,206 B2 | 12/2003 | Corcoran et al. | |
| 6,673,100 B2 | 1/2004 | Diaz et al. | |
| 6,692,458 B2 | 2/2004 | Forman et al. | |
| 6,749,622 B2 | 6/2004 | McGuckin, Jr. et al. | 606/213 |
| 6,752,826 B2 | 6/2004 | Holloway et al. | |
| 6,790,218 B2 | 9/2004 | Jayaraman | |
| 6,911,037 B2 | 6/2005 | Gainor et al. | 606/213 |
| 6,939,377 B2 | 9/2005 | Jayaraman et al. | 623/1.46 |
| 6,949,113 B2 | 9/2005 | Van Tassel et al. | 606/200 |
| 6,949,116 B2 | 9/2005 | Solymar et al. | |
| 6,974,474 B2 | 12/2005 | Pavcnik et al. | 623/1.24 |
| 6,994,092 B2 | 2/2006 | Van der Burg et al. | 128/887 |
| 6,994,717 B2 | 2/2006 | Konya et al. | |
| 7,101,381 B2 | 9/2006 | Ford et al. | 606/151 |
| 7,101,395 B2 | 9/2006 | Tremulis et al. | |
| 7,128,073 B1 | 10/2006 | Van der Burg et al. | |
| 7,288,105 B2 | 10/2007 | Oman et al. | 606/215 |
| 2001/0034537 A1 | 10/2001 | Shaw et al. | 606/213 |
| 2001/0037129 A1 | 11/2001 | Thill | 606/213 |
| 2001/0039450 A1 | 11/2001 | Pavcnik et al. | 623/1.24 |
| 2002/0111647 A1 | 8/2002 | Khairkhahan et al. | |
| 2002/0169475 A1 | 11/2002 | Gainor et al. | 606/213 |
| 2002/0183787 A1 | 12/2002 | Wahr et al. | 606/213 |
| 2002/0187288 A1 | 12/2002 | Lim et al. | |
| 2002/0198563 A1 | 12/2002 | Gainor et al. | |
| 2003/0028213 A1 | 2/2003 | Thill et al. | 606/200 |
| 2003/0093108 A1 | 5/2003 | Avellanet et al. | |
| 2003/0130713 A1 | 7/2003 | Stewart et al. | |
| 2003/0139819 A1 | 7/2003 | Beer et al. | |
| 2003/0144694 A1 | 7/2003 | Chanduszko et al. | |
| 2003/0149431 A1 | 8/2003 | Briana et al. | |
| 2003/0191495 A1 | 10/2003 | Ryan et al. | |
| 2003/0206860 A1 | 11/2003 | Bleyer et al. | |
| 2004/0073242 A1 | 4/2004 | Chanduszko | 606/157 |
| 2004/0078053 A1 | 4/2004 | Berg et al. | |
| 2004/0093017 A1 | 5/2004 | Chanduszko | |
| 2004/0098030 A1 | 5/2004 | Makower et al. | |
| 2004/0098042 A1 | 5/2004 | Devellian et al. | 606/213 |
| 2004/0133236 A1 | 7/2004 | Chanduszko | |
| 2004/0143277 A1 | 7/2004 | Marino et al. | 606/157 |
| 2004/0143291 A1 | 7/2004 | Corcoran et al. | 606/213 |
| 2004/0143292 A1 | 7/2004 | Marino et al. | 606/213 |
| 2004/0143293 A1 | 7/2004 | Marino et al. | |
| 2004/0143294 A1 | 7/2004 | Corcoran et al. | 606/213 |
| 2004/0166169 A1 | 8/2004 | Malaviya et al. | 424/551 |
| 2004/0176799 A1 | 9/2004 | Chanduszko et al. | 606/213 |
| 2004/0213756 A1 | 10/2004 | Michael et al. | 424/78.17 |
| 2004/0220596 A1 | 11/2004 | Frazier et al. | |
| 2004/0220610 A1 | 11/2004 | Kreidler et al. | |
| 2004/0230222 A1 | 11/2004 | Van der Burg et al. | 606/213 |
| 2004/0260340 A1 | 12/2004 | Jacobs et al. | |
| 2004/0267191 A1 | 12/2004 | Gifford, III et al. | |
| 2004/0267306 A1 | 12/2004 | Blaeser et al. | 606/213 |
| 2005/0010248 A1 | 1/2005 | Lafontaine et al. | |
| 2005/0034735 A1 | 2/2005 | Deem et al. | |
| 2005/0043759 A1 | 2/2005 | Chanduszko | 606/213 |
| 2005/0049634 A1 | 3/2005 | Chopra | 606/213 |

(56) References Cited

U.S. PATENT DOCUMENTS

| | | | |
|---|---|---|---|
| 2005/0065547 A1 | 3/2005 | Marino et al. | 606/213 |
| 2005/0065548 A1 | 3/2005 | Marino et al. | 606/213 |
| 2005/0070794 A1 | 3/2005 | Deal et al. | 600/434 |
| 2005/0070821 A1 | 3/2005 | Deal et al. | 600/585 |
| 2005/0085843 A1 | 4/2005 | Opolski et al. | |
| 2005/0125032 A1 | 6/2005 | Whisenant et al. | 606/213 |
| 2005/0125050 A1 | 6/2005 | Carter et al. | 623/1.11 |
| 2005/0192626 A1 | 9/2005 | Widomski et al. | 606/213 |
| 2005/0192627 A1 | 9/2005 | Whisenant et al. | 606/213 |
| 2005/0203568 A1 | 9/2005 | Burg et al. | |
| 2005/0228434 A1 | 10/2005 | Amplatz et al. | |
| 2005/0234509 A1 | 10/2005 | Widomski et al. | 606/213 |
| 2005/0249772 A1 | 11/2005 | Malaviya et al. | 424/423 |
| 2005/0251201 A1 | 11/2005 | Roue et al. | |
| 2005/0256532 A1 | 11/2005 | Nayak et al. | |
| 2005/0267524 A1 | 12/2005 | Chanduszko | 606/213 |
| 2005/0267526 A1 | 12/2005 | Wahr et al. | 606/213 |
| 2005/0273119 A1 | 12/2005 | Widomski et al. | 606/151 |
| 2005/0273124 A1 | 12/2005 | Chanduszko | 606/159 |
| 2005/0273135 A1 | 12/2005 | Chanduszko et al. | 606/213 |
| 2005/0283187 A1 | 12/2005 | Longson | 606/213 |
| 2005/0288706 A1 | 12/2005 | Widomski et al. | |
| 2005/0288786 A1 | 12/2005 | Chanduszko | |
| 2006/0009800 A1 | 1/2006 | Christianson et al. | 606/213 |
| 2006/0036282 A1 | 2/2006 | Wahr et al. | 606/213 |
| 2006/0052816 A1 | 3/2006 | Bates et al. | 606/200 |
| 2006/0052821 A1 | 3/2006 | Abbott et al. | 606/213 |
| 2006/0106418 A1 | 5/2006 | Seibold et al. | |
| 2006/0106420 A1 | 5/2006 | Dolan et al. | |
| 2006/0122646 A1 | 6/2006 | Corcoran et al. | 606/213 |
| 2006/0155327 A1 | 7/2006 | Briganti et al. | 606/213 |
| 2006/0200196 A1 | 9/2006 | Zang et al. | 606/213 |
| 2006/0201996 A1 | 9/2006 | Hodde | 228/101 |
| 2006/0210603 A1 | 9/2006 | Williams et al. | |
| 2006/0216326 A1 | 9/2006 | Pacetti | |
| 2006/0217760 A1 | 9/2006 | Widomski et al. | 606/213 |
| 2006/0217761 A1 | 9/2006 | Opolski | 606/213 |
| 2006/0229670 A1 | 10/2006 | Bates | 606/213 |
| 2006/0235467 A1 | 10/2006 | Devore | |
| 2006/0241687 A1 | 10/2006 | Glaser et al. | |
| 2006/0271030 A1 | 11/2006 | Francis et al. | |
| 2008/0091235 A1 | 4/2008 | Sirota | 606/215 |
| 2009/0062836 A1 | 3/2009 | Kurrus | |
| 2009/0062844 A1 | 3/2009 | Tekulve et al. | |

FOREIGN PATENT DOCUMENTS

| | | |
|---|---|---|
| EP | 1 281 355 B1 | 9/2005 |
| JP | 02-307480 | 12/1990 |
| WO | WO 93/10714 | 6/1993 |
| WO | WO 98/27868 | 7/1998 |
| WO | WO 2007/092274 A1 | 8/2007 |

OTHER PUBLICATIONS

Braun, M., et al., "*Transcatheter Closure of Patent Foramen Ovale (PFO) in Patients With Paradoxical Embolism*", European Heart Journal (2004), vol. 25, pp. 424-430.

Das, Gladwin S., et al., "*Experimental Atrial Septal Defect Closure With a New, Transcatheter, Self-Centering Device*", Circulation, vol. 88, No. 4, Part 1, Oct. 1993, pp. 1754-1764.

Heeschen, Christopher, et al., "*Nicotine Stimulates Angiogenesis and Promotes Tumor Growth and Atherosclerosis*", Nature Medicine vol. 7, No. 7, (Jul. 2001), pp. 833-839.

Johnson, Chad, et al., "*Matrix Metalloproteinase-9 is Required for Adequate Angiogenic Revascularization of Ischemic Tissues*", Circulation Research, Feb. 6, 2004, No. 94, pp. 262-268.

Jux, Christian, et al., "*A New Biological Matrix for Septal Occlusion*", Journal of Interventional Cardiology, vol. 16, No. 2, (2003), pp. 149-152.

Jux, Christian, et al., "*Interventional Atrial Septal Defect Closure Using a Totally Bioresorbable Occluder Matrix*", JACC, vol. 48, No. 1, (2006), pp. 161-169.

King, Terry D., et al., "*Secundum Atrial Septal Defect-Nonoperative Closure During Cardiac Catheterization*", JAMA, vol. 235, No. 23, Jun. 7, 1978, pp. 2506-2509.

Mullen, Michael J., et al., "*BioSTAR Evaluation STudy (BEST) A Prospective, Multicenter, Phase I Clinical Trial to Evaluate the Feasibility, Efficacy, and Safety of the BioSTAR Bioabsorbable Septal Repair Implant for the Closure of Atrial-Level Shunts*", Circulation, Oct. 31, 2006, pp. 1962-1967.

Pavcnik, Dusan et al., "*Monodisk: Device for Percutaneous Transcatheter Closure of Cardiac Septal Defects*", Cardiovasc Intervent Radiol (1993) vol. 16, pp. 308-312.

Rashkind, William J., "*Transcatheter Treatment of Congenital Heart Disease*", Circulation vol. 67, No. 4, Apr. 1983, pp. 711-716.

Sideris, E.B. et al., "*Transvenous Atrial Septal Defect Occlusion in Piglets with a "Buttoned" Double-Disk Device*", Circulation, vol. 81, No. 1, Jan. 1990, pp. 312-318.

"*Transcatheter Closure of Atrial Septal Defects*", The Lancet, Sep. 1, 1990, pp. 566-567.

Bhattathiri, VN, et al., "*Influence of plasma GSH level on acute radiation mucositis of the oral cavity*", International Journal of Radiation Oncology Biology Physics, (1994), vol. 29, No. 2, pp. 383-386.

Oguchi, M., et al., "*Mucosa-adhesive water-soluble polymer film for treatment of acute radiation-induced oral mucositis*", International Journal of Radiation Oncology Biology Physics, Mar. 15, 1998, vol. 40, No. 5, p. 1033-1037.

\* cited by examiner

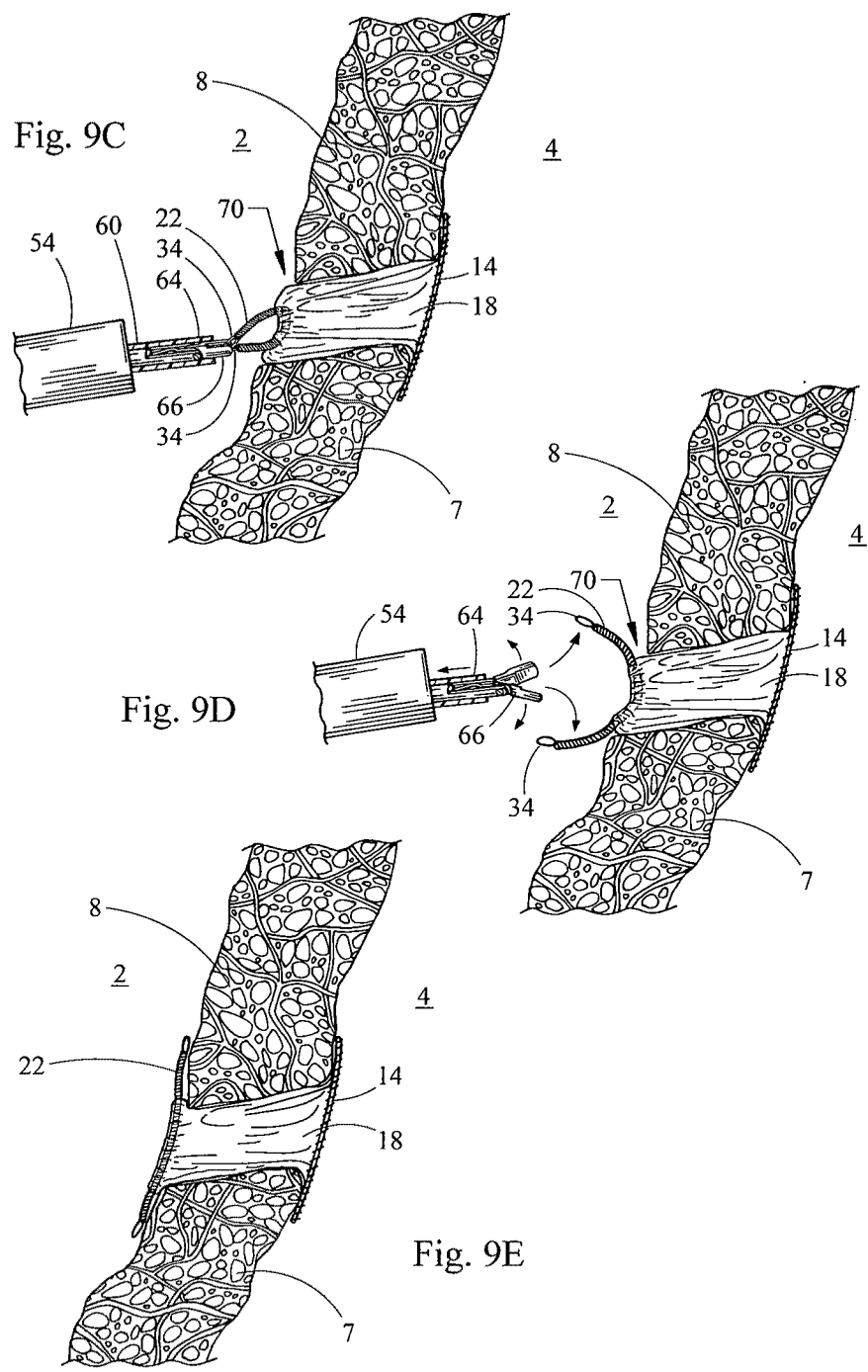

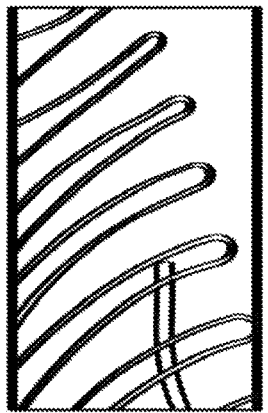
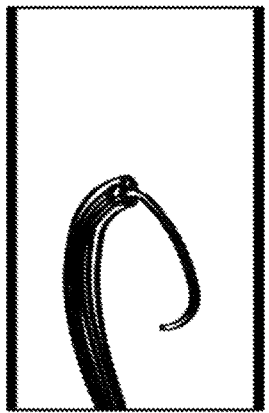
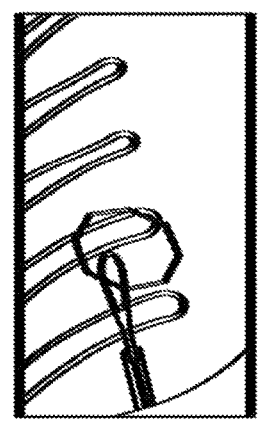
FIG - 10A   FIG - 10B   FIG - 10C
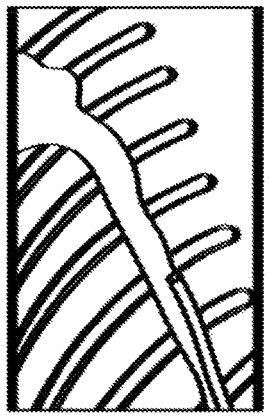
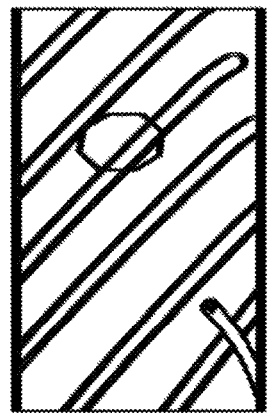
FIG - 10D   FIG - 10E

CLOSURE DEVICE AND METHOD OF CLOSING A BODILY OPENING

The present application is a continuation of PCT International Application Serial Number PCT/US2008/001422, filed Feb. 1, 2008, which designates the U.S. and was published in English, and which claims priority to U.S. Provisional Patent Application Ser. No. 60/60,898,834, filed Feb. 1, 2007, both of which are hereby incorporated by reference.

TECHNICAL FIELD

This invention relates generally to medical devices, and particularly, to implantable medical devices for closing bodily passageways, including the patent foramen ovale (PFO) and various atrial septal defects (ASDs).

BACKGROUND

A patent foramen ovale is a persistent, one-way, usually flap-like opening in the wall between the right atrium and left atrium of the heart. In utero, the foramen ovale serves as a physiologic conduit for right-to-left shunting of blood in the fetal heart. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

Where anatomical closure of the foramen ovale does not occur, a PFO is created. Studies have shown that a relatively large percentage of adults have a PFO. The presence of a PFO is generally considered to have no therapeutic consequence in otherwise healthy adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium to the left atrium and blood clots could enter the systemic circulation. It is desirable that this circumstance be eliminated.

Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. It has been estimated that in 50% of cryptogenic strokes, a PFO is present. In addition, there is significant evidence that patients with a PFO who have had a cerebral vascular event are at increased risk for future, recurrent cerebrovascular events.

Patients suffering a cryptogenic stroke or a transient ischemic attack (TIA) in the presence of a PFO often are considered for medical therapy to reduce the risk of a recurrent embolic event. Accordingly, patients at such an increased risk are considered for prophylactic medical therapy to reduce the risk of a recurrent embolic event. These patients are commonly treated with oral anticoagulants to reduce the risk of a recurrent embolic event. However, these anticoagulants have potentially adverse side effects, including hemorrhaging, hematoma, and adverse interactions with other drugs. In addition, use of anticoagulant drugs can alter a person's recovery and necessitate adjustments in a person's daily living pattern.

Where anticoagulation is contraindicated, surgery may be employed to close a PFO. The surgery would typically include suturing a PFO closed by attaching septum secundum to septum primum. Like other open surgical treatments, however, this surgery is highly invasive, risky, requires general anesthesia, and may result in lengthy recuperation.

Nonsurgical closure of PFOs has become possible with the introduction various mechanical closure devices, including umbrella devices and the like, which were initially for percutaneous closure of atrial septal defects (ASDs; a condition where there is not a septum primum). These devices potentially allow patients to avoid the side effects often associated with anticoagulation therapies and the risks of invasive surgery.

However, devices for treating heart defects, such as PFO and other atrial and ventricular septal heart defects have their share of drawbacks. The complex anatomical features of PFOs present a challenge to a one size fits all approach. The PFO involves two components, septum primum and septum secundum. The septum secundum is thicker than septum primum and exhibits limited mobility and compliance. Failure of these two structures to fuse creates a tunnel-like opening, the PFO. The distance of the nonfusion between the two septa determines the particular size of the PFO, which must be considered in the design of a device targeting PFOs. Nevertheless, devices are often configured so that the patient's anatomy must be adjusted to fit the geometry of the device. As a consequence, heart tissue may be torn when accommodating such devices.

Conventional nonsurgical closure devices are often technically complex, bulky, have a high septal profile, low radiopacity, and an inability to provide immediate closure. Additionally, many of the devices have a geometry which tends to prevent the device from remaining flat against, or within the defect once deployed. The varying passageway geometries often require multiple sized devices. Moreover, many devices are set apart by a relatively long central section corresponding to the PFO tunnel. By increasing the device profile, the device can present difficulties with respect to complete endothelialization. Conventional closure devices are often difficult to deploy or reposition, often require replacement or repositioning, and require relatively large delivery catheters (for example, 9-10 French or more). In addition, the large masses of foreign material associated with the device may lead to unfavorable body adaptation to the device, including thromboses or other unfavorable reactions. Further drawbacks to nonsurgical closure devices include complications resulting from fractures of the components, conduction system disturbances, perforations of heart tissue, residual leaks, and inability to allow subsequent methods involving transeptal puncturing.

Accordingly, there is a need for improved low profile closure devices and simplified delivery methods for immediate closure, which are capable of limiting the amount of foreign material deployed and enhancing closure stability. The present invention is designed to address a number of the deficiencies surrounding conventional closure devices.

SUMMARY

In one embodiment, a closure device for closing or occluding a bodily passageway, such as a PFO, includes a circumferential frame, a sheet of biocompatible material attached to the frame, and at least one anchor attached to the sheet of biocompatible material. The anchor may be formed from at least one flexible, substantially linear structure in the form of a tube, coil, bar, or wire. The anchor includes at least one grasping member projecting away from one or more anchor ends to facilitate delivery of the device. The grasping member may include a loop structure integral with the linear structure or disposed on a second structure separate from and connected to the tube, coil, bar, or wire. In particular, the anchor may be formed from an anchor coil having an anchor wire extending longitudinally therethrough. The anchor wire may be formulated to include at least one terminally disposed grasping member frictionally engaged by the anchor coil. One or more grasping members may be attached to a closure device engaging member (such as a biopsy forceps) facilitating delivery of the device.

In another embodiment, the closure device includes a circumferential frame; a crossbar extending across the frame, the crossbar having crossbar ends connected to discontinuous sites on the circumferential frame; at least one anchor connected to at least one crossbar; and at least one sheet or layer of biocompatible material (such as ECM material) attached to the frame. In addition to being attached to the frame, the sheet or layer of biocompatible material may be additionally attached to at least a portion of at least one crossbar or to the length of the crossbar in its entirety.

Each of the frame, crossbar(s), and anchor(s) includes at least one flexible, substantially linear structure in the form of a tube, coil, bar, or wire. In one embodiment, each of the frame, crossbar(s), and anchor(s) is formed from at least one flexible, substantially linear coil. One or more wires may be used for interconnecting the frame, crossbar(s) and anchor(s).

In one embodiment, a central portion of at least one crossbar is connected to a central portion of at least one anchor. In this case, the anchor ends may be connected to one another by a delivery bar. The delivery bar includes at least one flexible, substantially linear structure in the form of a tube, coil, bar, or wire as described herein. A delivery bar may be used to enhance the deployment, repositioning, and retrieval of closure devices according to the present invention.

In another embodiment, two crossbars are connected to the frame and two anchors are connected to the crossbars, each anchor being connected to a different crossbar. In one embodiment, a central portion of each crossbar is connected to a central portion in one of the two anchors. The crossbar ends may be linked or unlinked. Where the crossbar ends are linked, a pair of oppositely positioned linked anchor ends may be connected to one another by a delivery bar as described herein.

The device may further include a plurality of terminal grasping members projecting away from the anchor ends to aid in device delivery, device connectivity, or both. In one embodiment, each anchor is formed from an anchor coil having an anchor wire extending longitudinally therethrough. The grasping members may include a loop structure integral with the linear anchor or they may be disposed on a secondary structure, such as a wire extending through an anchor longitudinally and configured to form at least one terminally disposed grasping member frictionally engaged by the anchor. One or more grasping members may be attached to a delivery release member (such as a biopsy forceps) facilitating delivery of the device.

Frictionally engaged terminally disposed grasping members may also be incorporated into one or more ends of the crossbar, anchor, and/or delivery bar to facilitate connectivity and enhanced swivelability therebetween. For example, closed loops at the crossbar, anchor, or delivery bar ends can be used to interconnect one or more of these elements to one another. The closed loops can be formed, for example, from wires extending longitudinally through hollow structures, including coils, as described above. The interconnected loops can provide enhanced collapsibility, expandability, and swivelability of the various component parts relative to one another. In addition, the interconnected loops can help to better conform the device to the architectural nuances unique to a given bodily passageway.

In another aspect, a closure device assembly for delivering any of the disclosed closure devices is provided. In one embodiment, the assembly includes a delivery catheter housing a delivery release member, and a collapsibly disposed closure device according to the invention, whereby at least one anchor or delivery bar in the closure device is releasably connected to the delivery release member.

In one embodiment, the delivery release member includes a complementary structure (including for example, biopsy jaws or cups) to facilitate releasable linkage to at least one grasping member in the anchor, such as a loop. In another embodiment, the delivery release member includes a complementary structure, such as a hook, to facilitate releasable linkage to a flexible delivery bar connected between one or more pairs of anchor ends. One or more grasping members may be terminally disposed on one or more anchors. The delivery release member may include one or more structural portions for releasable attachment to an anchor or delivery bar. Accordingly, the delivery release member may include an anchor engaging portion or a delivery bar engaging portion, including at least one structure selected from the group consisting of hook, ball, loop, cup, jaw or combination thereof. Upon disengagement of the anchor grasping member or delivery bar from the delivery release member, for example, the covered frame of sheet material can be released so as to cover an opening of the bodily passageway, whereby one or more anchors are secured to the opposite end of the bodily passageway, thereby sandwiching the device around and through a bodily passageway, such as a PFO.

In a further aspect, a closure device assembly includes a delivery catheter houses a locking catheter housing the delivery release member. The locking catheter is secured to the anchor release member so that the closure device is prevented from being released inside of the delivery catheter. In particular, at least one anchor or delivery bar is connected to the delivery release member in a locking catheter configured to prevent the delivery release member from releasing the anchored closure device inside of the delivery catheter unless the locking catheter sheath is retracted. The assembly may preferably employ a 6, 7, 8 or 9 French delivery catheter and a 3, 4, 5 or 6 French locking catheter, whereby the assembly is configured for releasable attachment of a collapsibly disposed closure device to a delivery release member in the delivery catheter.

In a further aspect, the present invention provides a method for closing or occluding a bodily passageway, such as a PFO, using any of the closure device assemblies described herein. Briefly, the delivery catheter of the closure device assembly may be positioned through a bodily passageway of a patient proximate to first opening of the bodily passageway. Following release of the covered frame therein, the delivery catheter may be retracted through the bodily passageway, positioning the delivery catheter proximate to a second opening of the bodily passageway. At this point, an anchor or delivery bar may be disengaged from the delivery release member, thereby releasing the anchor or delivery bar proximate to the second opening of the bodily passageway. As a result, the closure device is secured to tissue portions surrounding the bodily opening, thereby closing the bodily opening.

In a preferred method, a closure device assembly of the present invention is used to close a septal defect, such as PFO. In particular, the delivery catheter of the closure device assembly may be positioned in the left atrium of patient proximate to distal PFO opening. Following release of the covered frame into the left atrium, the delivery catheter may be retracted through the PFO into the right atrium, positioning the delivery catheter proximate to the proximal PFO opening. At this point, an anchor or delivery bar may be disengaged from the delivery release member, thereby releasing the anchor proximate to the proximal PFO opening. As a result, the closure device is secured to tissue portions surrounding the bodily opening, thereby closing the bodily opening. Deployment of the closure device can produce immediate and complete closure of the bodily passageway. The closure device is preferably configured so that the device can be repositioned during the deployment process or to permit removal using a snare or other suitable removal device.

BRIEF DESCRIPTION OF THE DRAWINGS

FIG. 9C illustrates a cross-sectional view of the distal end of the closure device assembly of FIG. 7B showing attachment of the anchor to the biopsy forceps and positioning of the anchor on the proximal side of the PFO opening.

FIG. 9D illustrates a cross-sectional view of the distal end of the closure device assembly of FIG. 7B showing retraction of the locking catheter sheath and disengagement of the anchor from the biopsy forceps.

FIG. 9E illustrates a cross-sectional view illustrating a deployed closure device closing a PFO.

FIG. 10A is a right atrial venogram indicating a PFO of 5-6 mm.

FIG. 10B is a venogram showing a delivery catheter carrying a compressed, tip-preloaded closure device being advanced over a guide wire through a PFO into the left atrium.

FIG. 10C is a venogram showing a delivery catheter releasing a closure device whereby the covered frame is pulled against the septum primum and the septum secundum, positioning the radiopaque anchor in the right atrium proximate to the proximal PFO opening.

FIG. 10D depicts subtraction right atrial venography (in lateral view) showing complete, immediate closure of the PFO.

FIG. 10E depicts a chest X-ray (in lateral view) showing the radiopaque closure device after implantation.

DETAILED DESCRIPTION

Figure 1:
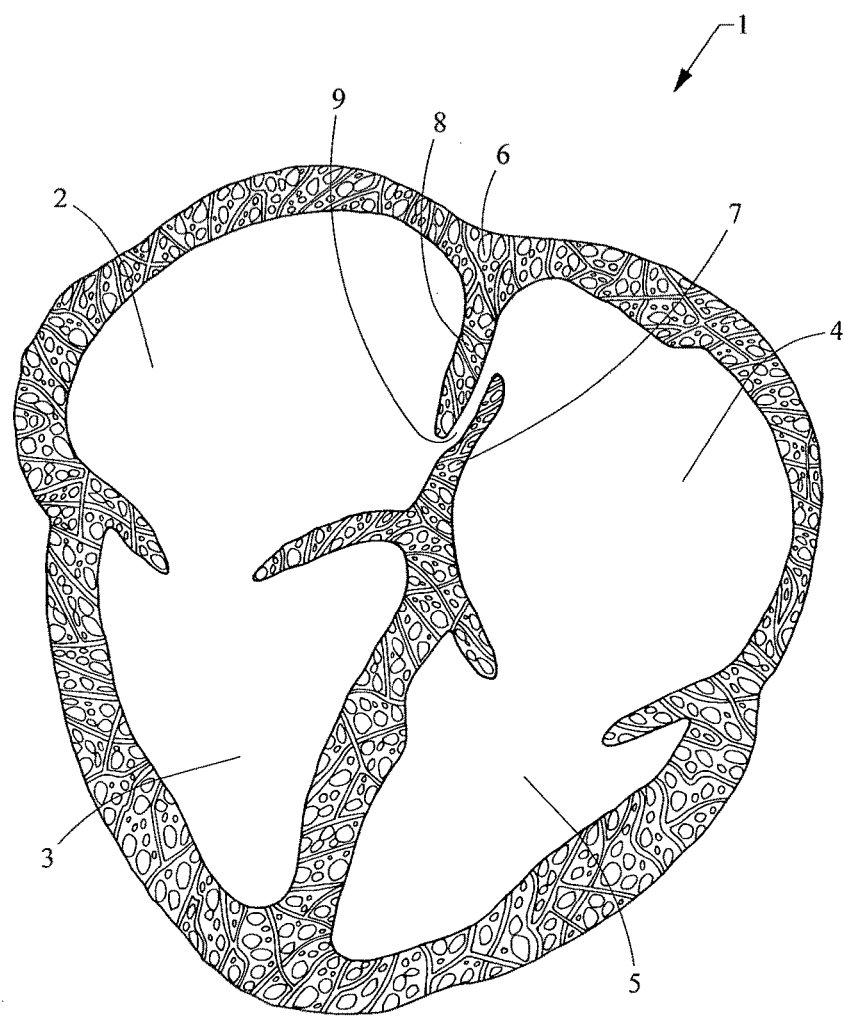
FIG. 1 illustrates a cross-sectional view of a heart with a PFO.

A closure device for closing or occluding bodily passageways, including septal openings of the heart is provided.

Unlike certain other PFO closure devices in the prior art, the closure device of the present invention can provide reduced foreign materials, a low profile, self-centering capacity, good radiopacity, simplified delivery, and an increased capacity for immediate closure of a variety of passageway sizes. Without wishing to be bound by a particular theory or to in any way limit the scope of the appended claims and their equivalents, it is believed that incorporation of bioremodelable material capable of causing angiogenesis and replacement by host tissues according to the present invention provides a more stable and permanent closure compared to conventional closure devices.

In order to provide a clear and consistent understanding of the specification and claims, the following definitions are provided.

As used herein, the terms "opening", "bodily opening", "passageway", and "bodily passageway" are interchangeably used to refer to a bodily opening, aperture, canal, conduit, or duct, including but not limited to septal openings, heart valves, blood vessels, vessel punctures, bile ducts, and the like.

The terms "connected", "connecting", "connectively linked" and "connectively linking" interchangeably refer to the joining, adhering, bonding, attaching, or the like, of two elements. Two elements will be considered to be connected together when they are connected directly to one another or indirectly to one another, such as when each is directly connected to intermediate elements.

The term "anchor" refers to a flexible, substantially linear structure in a closure device of the present invention, which is configured to be positioned on a side of a bodily passageway so as to anchor a covered frame positioned on the opposite side of the bodily passageway.

The term "grasping member" refers to a grasping structure on the device having a shape suitable (for example, loop, knob, ball, hook, and the like) for releasable attachment to a delivery release member. The grasping member may be integral with a tube, coil, bar, or wire in an anchor or delivery bar or it may be disposed on a second structure separate from and connected to the tube, coil, bar, or wire. The grasping member may in the form of a closed loop (in for example, a wire) or as a graspable portion of a flexible linear structure, such as a coil.

The term "delivery release member" refers to a structural component in a delivery device assembly for facilitating releasable delivery of the closure device by releasable attachment to a portion of the closure device, such as an anchor or delivery bar.

The term "anchor release member" refer to a delivery release member facilitating releasable delivery of the closure device by releasable attachment to at least one anchor grasping member. An anchor release member includes one or more complementary structures configured for linkage and releasable attachment to an anchor grasping member.

The terms "central portion of the frame", "central portion of the crossbar", and "central portion of the anchor" are used interchangeably with reference to positions which are not more than about 30% away from a structural component's geometric center.

As used herein, the term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "bioresorbable" refers to refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

As used herein, the term "bioremodelable" refers to a natural or synthetic material that is bioresorbable and capable of inducing angiogenesis, tissue remodeling, or both in a subject or host. A bioremodelable material includes at least one bioactive agent capable of inducing angiogenesis or tissue remodeling. One or more bioactive agents in the bioremodelable material may stimulate infiltration of native cells into an acellular matrix, and formation of new blood vessels (capillaries) growing into the matrix to nourish the infiltrating cells (angiogenesis). Additionally, the bioactive agents may effect the degradation or replacement of the bioremodelable material by endogenous tissue. The bioremodelable material may include a naturally derived collagenous ECM tissue structure present in, for example, native submucosal tissue sources, including, but not limited to small intestine submucosal (SIS) tissue, or it may include any one of a variety of different non-submucosal ECM-containing tissue materials or synthetic, bioresorbable non-ECM materials capable of inducing angiogenesis and tissue remodeling in a host.

The phrases "sheet of biocompatible material" and "sheet of bioremodelable material" refer to one or more biocompatible or bioremodelable tissue layers or synthetic polymeric layers formed into a sheet or composite thereof. A sheet of biocompatible or bioremodelable material may include, for example, one or more naturally-derived tissue layers containing an ECM scaffold, one or more biocompatible polymeric layers, or combinations thereof. The sheet of biocompatible or bioremodelable material can be in the form of a single tissue or polymeric layer or a plurality of tissue or polymeric layers in form of laminates, composites, or combinations thereof.

The terms "angiogenesis" and "angiogenic" refer to bioactive properties, which may be conferred by a bioremodelable material through the presence of growth factors and the like, which are defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other closure devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

The term "radiopaque" refers to a non-toxic material capable of being monitored or detected during injection into a mammalian subject by, for example, radiography or fluoroscopy. The radiopaque material may be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum.

In one embodiment, a closure device for closing or occluding a bodily passageway, such as a PFO, includes a circumferential frame, a sheet of biocompatible material at least partially or substantially covering the frame, and one or more anchors connected to the sheet of biocompatible material. The anchor may include a tube or coil which is connected to a grasping member having a structure (such as a loop) suitable for releasable attachment to a delivery release member facilitating delivery of the closure device.

FIG. 1 is a schematic front view of a heart 2 with a septal defect, such as patent foramen ovale (PFO). The heart 1 has a right atrium 2, right ventricle 3, left atrium 4, and a left ventricle 5. The septum 6 between the right atrium 2 and the left atrium 4 comprises a septum primum 7 and a septum secundum 8. The PFO 9 is an opening in the septum 6 that has not properly closed. Where a PFO 9 is present, the septum primum 7 typically overlaps the septum secundum 8 and the higher pressure in the left atrium 4 typically closes the flaps of the septum primum 7 and the septum secundum 8 so that blood does not leak between the atria 2 and 4. However, when there is a pressure change in the chest, the flaps may separate permitting blood to flow through the PFO and between the atria 2 and 4.

Figure 2A:
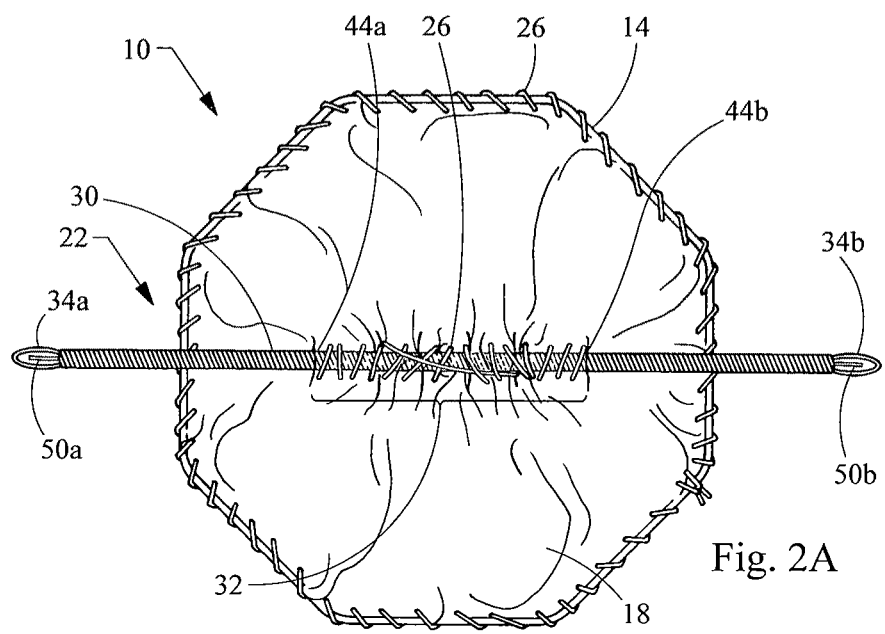
FIG. 2A illustrates a plan view of an exemplary closure device according to an embodiment of the present invention.
Figure 2B:
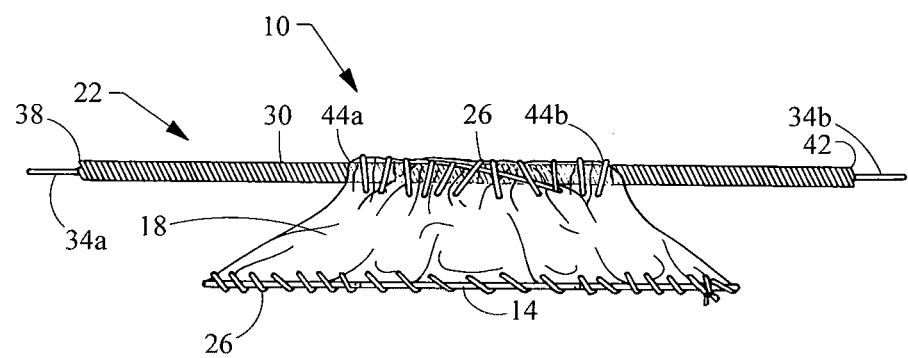
FIG. 2B illustrates a side view of the embodiment depicted in FIG. 2A.

FIGS. 2A and 2B show a closure device 10 depicting aspects of the present invention, including a circumferential frame 14, a sheet 18 of biocompatible material covering the frame 14, and an anchor 22 connected to the sheet 18 of biocompatible material. The circumferential frame 14 defines a plane which is at least partially covered by the sheet 18 of biocompatible material. Preferably the frame 14 is substantially covered or completely covered by the sheet 18 of biocompatible material. The sheet 18 of biocompatible material provides a covering over the circumferential frame 14, which is designed to cover or occlude a bodily passageway.

The frame 14 may be configured in any substantially closed, planar shape or geometry suitable for supporting a sheet 18 of biocompatible material for covering or occluding a septal opening, such as a PFO. The frame 14 is defined by a planar structure having straight or curved edges, which may be configured into the form of a polygonal, circular, or elliptical shape. The frame 14 may have straight or curved edges. The frame may be in the form of a closed or substantially closed wire, coil, tubular structure, or bar-like structure. The frame 14 may be discontinuous, provided that is capable of supporting a sheet 18 of biocompatible material onto a frame configuration suitable for covering a septal opening, such as a PFO. Exemplary polygonal shapes include, but are not limited to triangle, quadrilateral, square, pentagon, hexagon, octagon, and the like. Circular shapes include circle, oval, ellipse, and the like. FIG. 2A depicts an exemplary frame 14 that is shaped in the form of a wired octagon.

Generally, the frame 14 has a first configuration wherein the sides and bends generally lie within a single, flat plane, and a second configuration whereby sides and bends are brought in closer proximity to one another when the frame 14 is collapsibly disposed in a delivery catheter. In one aspect, the frame 14 is formed from one or more wires, tubular members, coils, or bars. The frame 14 may be formed from a variety of wire materials differing in shape and material substance. For example, the frame 14 may be formed from flat or rounded wires having a variety of cross-sectional shapes (for example, oval, delta, D-, and the like). The frame 14 may be formed from a single piece of wire or other material having a plurality of sides and bends each interconnecting adjacent sides. A closed circumferential frame may be formed a single piece of continuous, circumferential wire or it may be joined by any suitable attachment mechanism, including, but not limited to cannula and solder, spot welding, and the like.

Additionally, the frame 14 may be formed from one or more linked coils or laser cut from a tube or bar. Generally, the frame will be formed from metallic material, such as platinum, stainless steel or Nitinol. The tube or bar may be hollow or filled. Additional methods for forming or manipulating a circumferential frame 14 are described in described in U.S. Patent Application Publication No. 2001/0039450 A1, the disclosures of which are expressly incorporated by reference herein.

When using frames 14 that are formed from coils or hollow tubular members, wires, threaded materials, sutures, adhesives or metallic couplers may be used to join the coil or hollow tubular member ends. Alternatively, the ends may be directly joined to one another by soldering or welding. Alternatively, the frame 14 may be prefabricated as a continuous closed structure. The use of a coil in a frame 14 can provide additional flexibility for repositioning or removal of the closure 10 device when using snares or other suitable removal or retrieval devices known to those of skill in the art.

The frame 14 may be variably sized depending on the size of the bodily passageway or septal opening, such as a PFO. In particular, the frame 14 is configured to completely overlap the opening at one end of the bodily passageway. Accordingly, the frame 14 may be configured with a diameter size or (diagonal size for polygonal frames) between about 5 mm and about 50 mm, preferably between about 10 mm and about 30 mm, or between about 15 mm and about 25 mm. By way of example, a frame 14 having a diameter size (or diagonal size for polygonal frames) between about 18 and about 20 mm may be used for closing most PFOs, while a size between about 25 and about 30 mm may be used for closing PFOs and other septal defects. Accordingly, the frame 14 may be configured with a diameter size ranging from about 15 to about 35 mm, preferably between about 18 to about 30 mm.

The frame 14 is at least partially or substantially covered by a sheet 18 of biocompatible material covering. Bioremodelable materials, including collagenous ECM materials and intestinal submucosal tissue materials, provide a preferred source of biocompatible sheet 18 materials for attachment to the frame 14 and are described in further detail below. ECM sheet materials or bioremodelable sheet materials formed from one or more layers of intestinal submucosal tissue are particularly preferred sources of bioremodelable materials for covering the frame 14. However, other biocompatible sheet 18 materials may be used in place of bioremodelable sheet material, including composites thereof. Exemplary biocompatible sheet materials include natural or synthetic polymeric or fibrous sheet materials, including DACRON, polytetrafluoroethylene (PTFE), expanded polytetrafluoroethylene (ePTFE), cotton, silk, wool, polyester, combinations thereof, and the like, which are further described below.

The sheet 18 of material preferably includes a flexible, pliable material configured onto the frame 14 to project into a passageway, substantially conforming to one or more portions defining the passageway. The sheet 18 may be sized or pre-stretched in accordance with a variety of desired three dimensional conformations, shapes, depths, and sizes suitable for closing or occluding a bodily passageway. In FIG. 2B, the sheet 18 has a domed conformation in a noncompressed state. Alternatively, the sheet 18 may be laid flat over the frame 14. Preferably the sheet 18 of material is applied to the frame 14, whereby the cross-sectional area of the sheet 18 material is greater than the cross-sectional area of the frame 14. Thus, the sheet 18 of material may be configured to take on a three dimensional conformation when deployed. Depending on the configuration of its attachment to elements of the closure device, the sheet 18 of biocompatible material can adapt itself to a variety of bodily passageway shapes and sizes.

The sheet 18 of biocompatible or bioremodelable material may be attached to the frame 14 by any suitable attachment method. In a preferred embodiment, the sheet 18 of biocompatible of bioremodelable material is attached by sutures 26. Alternative attachment methods include, but are not limited to, use of biological adhesives, use of chemical cross-linking agents, crimping, tissue welding, heat welding, pressure welding, heat source, light source, radiofrequency, lasering, other energy sources, and the like. Methods for attaching sheet materials to frames are described in U.S. Patent Application Publication No. 2001/0039450 A1, the disclosures of which are expressly incorporated by reference herein.

The anchor 22 refers to a flexible, substantially linear structure in a closure device of the present invention which is configured to be positioned on a side of a bodily passageway so as to anchor a covered frame 14 positioned on the opposite side of the bodily passageway. The anchor 22 is defined by a longitudinal structure having two ends, which extends over some or all the plane of the covered frame 14. In some embodiments, the anchor 22 extends beyond the periphery of the covered frame 14. The anchor 22 may be configured to include a substantially one-dimensional tube, coil, bar, or wire having two ends and a circular, elliptical or polygonal cross-sectional shape. The anchor 22 may be solid or hollow in nature.

In one aspect, an anchor 22 may include at least one grasping member 34 having a grasping structure or shape suitable (for example, loop, knob, ball, hook, and the like) for releasable attachment to a delivery release member facilitating delivery of the closure device 10. The grasping member 34 may be integral with the tube, coil, or bar, or it may include a separate structure engaged therewith. The grasping member 34 may be positioned at any anchor 22 site suitable for delivery of the closure device 10.

A delivery release member may include a structure configured for releasable attachment to one or more grasping members 34 in the closure device 10. The delivery release member may be configured as an anchor engaging member or anchor release member having an anchor engaging structure complementary to the grasping member 34 for releasable attachment thereto. The anchor engaging portion may include a ball, hook, loop, pair of cups or jaws, or any other suitable member capable of releasable attachment to a grasping member 34. In one embodiment, the anchor release member includes biopsy forceps. In another embodiment, the anchor release member includes one or more hook-release structures.

FIGS. 2A and 2B depict an exemplary anchor in the form of a linear coil connected to two terminally disposed grasping members 34 configured for releasable attachment to an anchor release member facilitating delivery of the device 10. In FIG. 2A, grasping members 34 are depicted as loop structures 34 formed from an anchor wire 46, which are frictionally engaged by the anchor coil 30 at both anchor coil ends 38, 42. Accordingly, in this embodiment the grasping members 34a, 34b represent structures separate from that of an anchor coil 30. Together, the anchor coil ends 38, 42 and the grasping member 34a, 34b define the anchor 22 ends.

Figure 3:
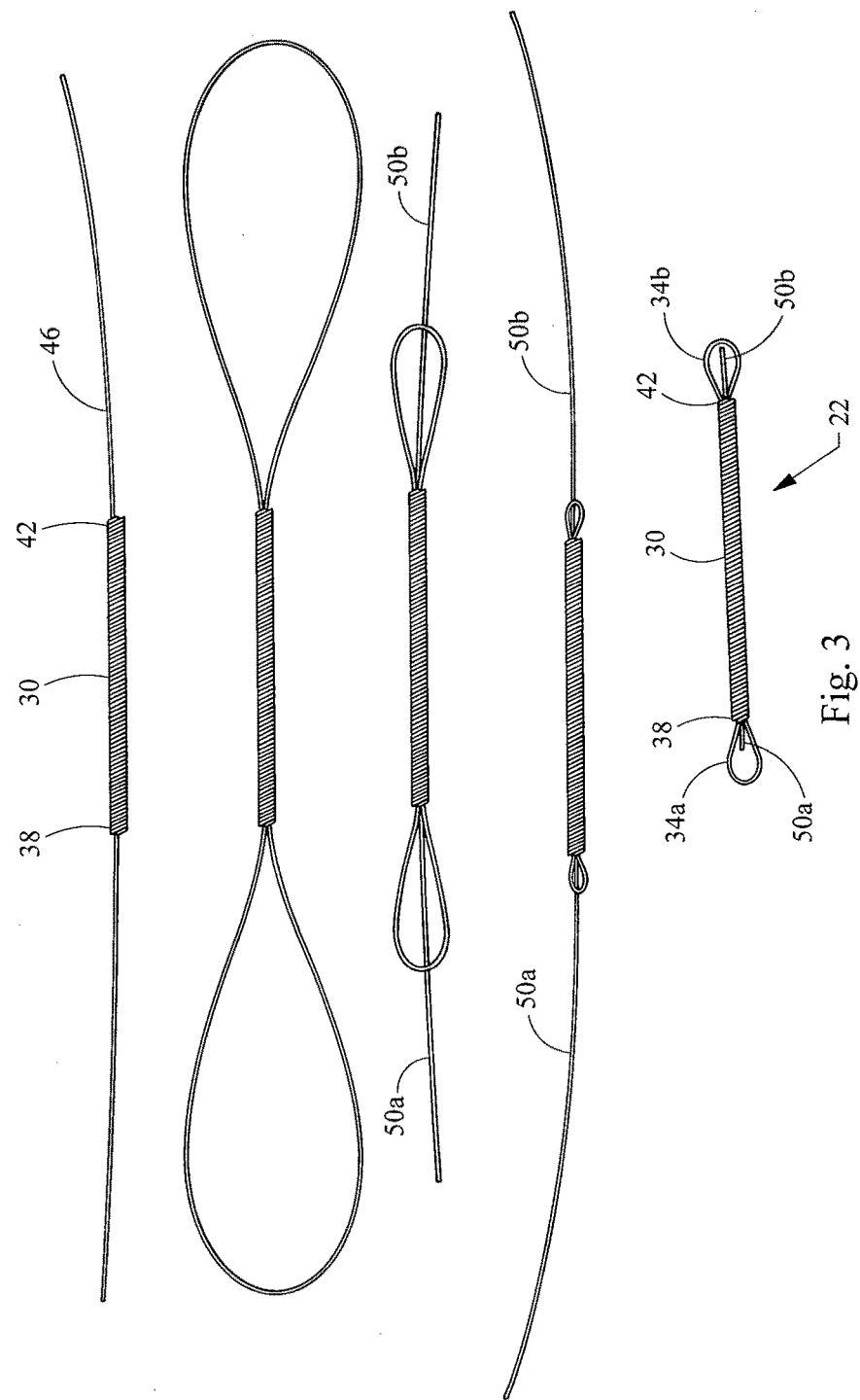
FIG. 3 illustrates a method for forming an anchor structure according to an aspect of the present invention.

FIG. 3 depicts a process for forming an anchor 22 as depicted in FIGS. 2, 4, and 5. Briefly, an anchor wire 46 is passed through an anchor coil 30 three times. The loop structures 34 can be formed by extending an anchor wire 46 through the anchor coil 30, looping the anchor wire 46 back towards each open anchor coil end 38, 42, pulling the anchor wire 46 at each anchor coil end 38, 42 back through the anchor coil 30 in the opposite direction to achieve a desired loop size, and cutting off the excess free anchor wire ends 50a, 50b extending from each anchor coil end 38, 42. The free anchor wire ends 50a, 50b may be looped back, knotted or crimped near the anchor coil ends 38, 42 to stabilize the terminally disposed loop structures 34 or free wire ends 50a, 50b proximal to each anchor coil end 38, 42. By configuring the loop structures 34 to be wider than the anchor coil 30 diameter at each anchor coil end 38, 42, the grasping members or loop structures 34 are frictionally engaged by or secured by the anchor coil 30.

One or more anchors 22 may be connected to the sheet 18 of biocompatible or bioremodelable material using any suitable method of attachment. The anchors 22 may be attached using sutures, clips, wires, staples, adhesives, combinations thereof, or any other suitable attachment materials or attachment structures known to those of skill in the art. Preferably, the anchors are at least attached to a central portion of the sheet 18, preferably so that at least a portion of the anchor 22 or the geometric center of a plurality of substantially parallel anchors 22 is positioned over a substantially central portion of the sheet 18. More particularly, one or more anchors 22 may be attached so that at least a portion of the anchor 22 or the geometric center of a plurality of substantially parallel anchors 22 is not more than 30% away from a sheet position corresponding to the geometric center of a covered frame 14. A plurality of anchors 22 may be connected to the sheet 18 for additional anchoring or support.

An anchor 22 may be attached so it traverses the plane of the sheet 18 material in one or more places or so that it closely adheres to one side of the sheet 18. In FIGS. 2A and 2B, the anchor 22 traverses the plane of the sheet 18 in two places 44a, 44b. In this case, the two points of traversal, 44a, 44b constitute a region of attachment 32 between the sheet 18 and the anchor 22. The attachment region 32 may be defined by a gap distance, d, in this case, between the two traversal points 44a, 44b. The attachment region 32 may help to define the configuration of sheet material when deployed. Sutures 26 may be used to securely link one or more anchors 22 to the sheet 18 over the attachment region. Portions of the anchor coil 30 may be partially stretched, creating small gaps in the anchor coil 30, which can serve to enhance the engagement between the sutures 26 and the anchor coil 30.

The inventors of the present invention have unexpectedly found that a gap distance of about 8 to about 9 mm in a 20 mm diameter octagon-shaped frame 14 allows good self-centering, anchoring, and immediate closure for a variety of passageway sizes, including small (2-4 mm), medium (5-8 mm) and large (9-13 mm) bodily passageways, including those found in PFOs.

In other aspects of the present invention, the closure device may further include one or more crossbars and a delivery bar. A crossbar extends across the frame, the crossbar having crossbar ends connected to discontinuous sites on the circumferential frame. The use of a crossbar has been found to enhance retrieval and collapsibility of the device, and absorb or relieve stretching forces (and possible tearing) that might otherwise adversely impact on the structural integrity of the biocompatible material. Further, the use of a delivery bar has been found to enhance delivery, repositioning and retrieval of the device.

Figure 4A:
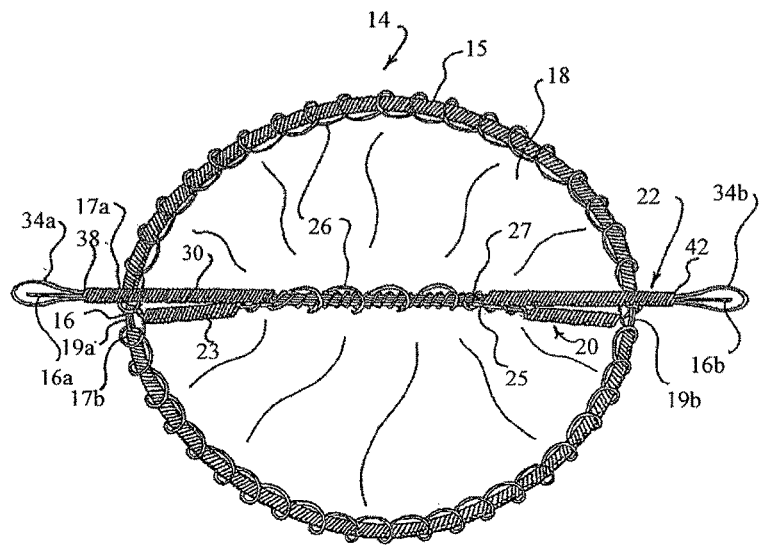
FIG. 4A illustrates a plan view of an exemplary closure device according to another embodiment of the present invention.
Figure 4B:
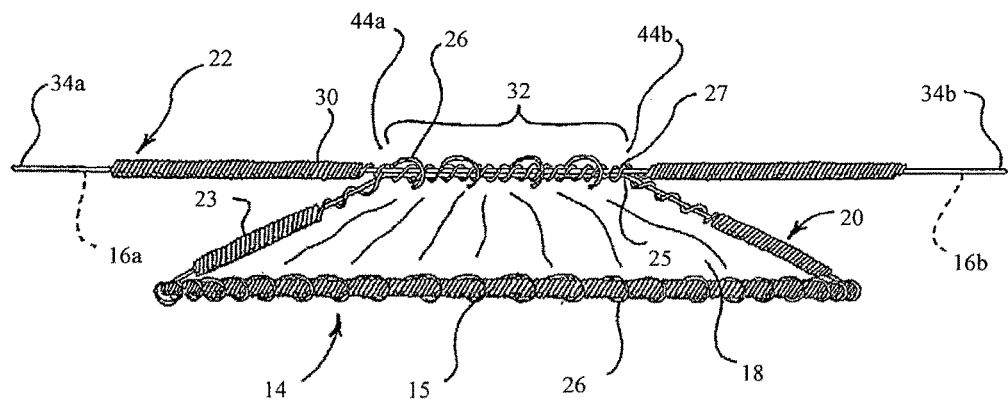
FIG. 4B illustrates a side view of the embodiment depicted in FIG. 4A.

FIGS. 4A and 4B depict an exemplary closure device in which a single crossbar 20 is connected to the frame 14, and a single anchor 22 is connected to the crossbar 20. FIGS. 5A to 5E depict an exemplary closure device in which two crossbars 20 are connected to the frame 14, and two anchors 22 are connected to the crossbars 20, each anchor 22 connected to a different crossbar 20.

The crossbar 20 is defined by a longitudinal structure having two ends, which extends over some or all the plane of the covered frame 14. Generally, one or more crossbars 20 may be connected by their ends 19a, 19b to discontinuous sites on the frame 14, typically at sites opposite to one another on the frame 14. Two crossbar ends 19a, 19b are connected to discontinuous sites on the frame 14, typically at frame 14 sites opposite to one another. The crossbar ends 19a, 19b may be linked or unlinked to one another.

The crossbar 20 is connected to at least a portion of an anchor 22. As depicted in FIGS. 4 and 5, a central portion in at least one crossbar 20 may be connected to a central portion in at least one anchor 22. When using a plurality of crossbars 20, a central portion in each crossbar may be connected to a central portion in any one of a plurality of anchors 22. The coupling between the crossbars 20 and the anchors 20 creates a symmetric center positioned within a bodily passageway upon deployment, the covered frame 14 and crossbars 20 being oriented toward a distal side of a bodily passageway in, for example, the left atrium 4, the anchors 22 and/or delivery bars 36 being oriented toward a proximal side of a bodily passageway in, for example, the right atrium 2 as depicted in FIG. 5C. Crossbars 20 may be oriented in the same longitudinal direction as the anchors 22. Alternatively, the crossbars 20 may be perpendicularly oriented relative to the anchors 22.

Figure 5A:
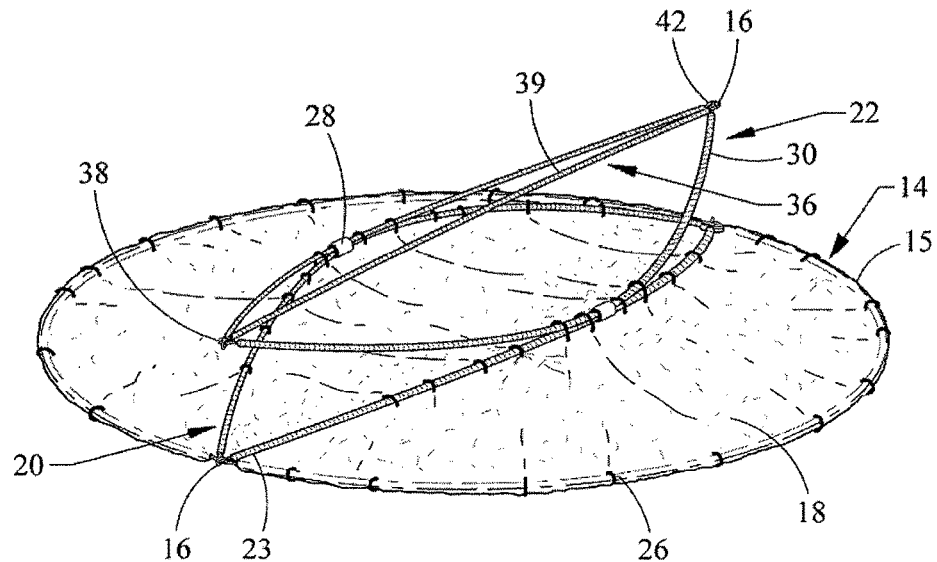
FIG. 5A illustrates a side view of an exemplary closure device according to another embodiment of the present invention.
Figure 5B:
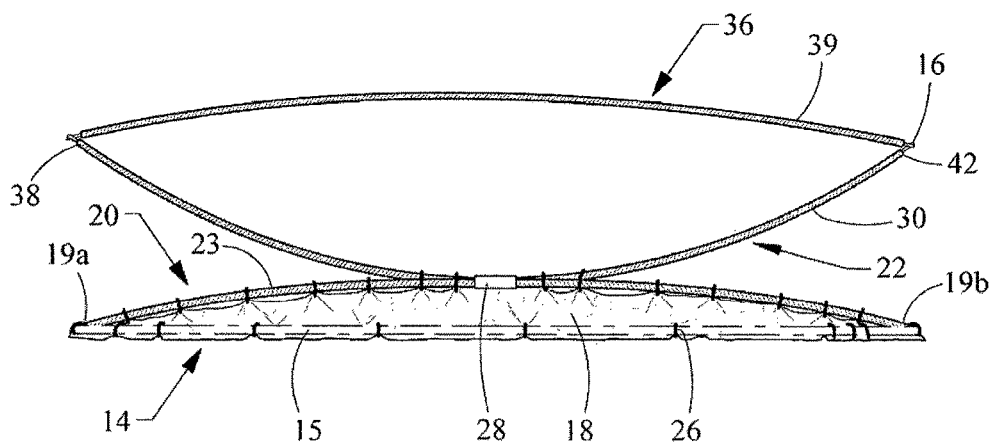
FIG. 5B illustrates a side view of the embodiment depicted in FIG. 5A modified to show a different pattern of biocompatible material attachment.
Figure 5C:
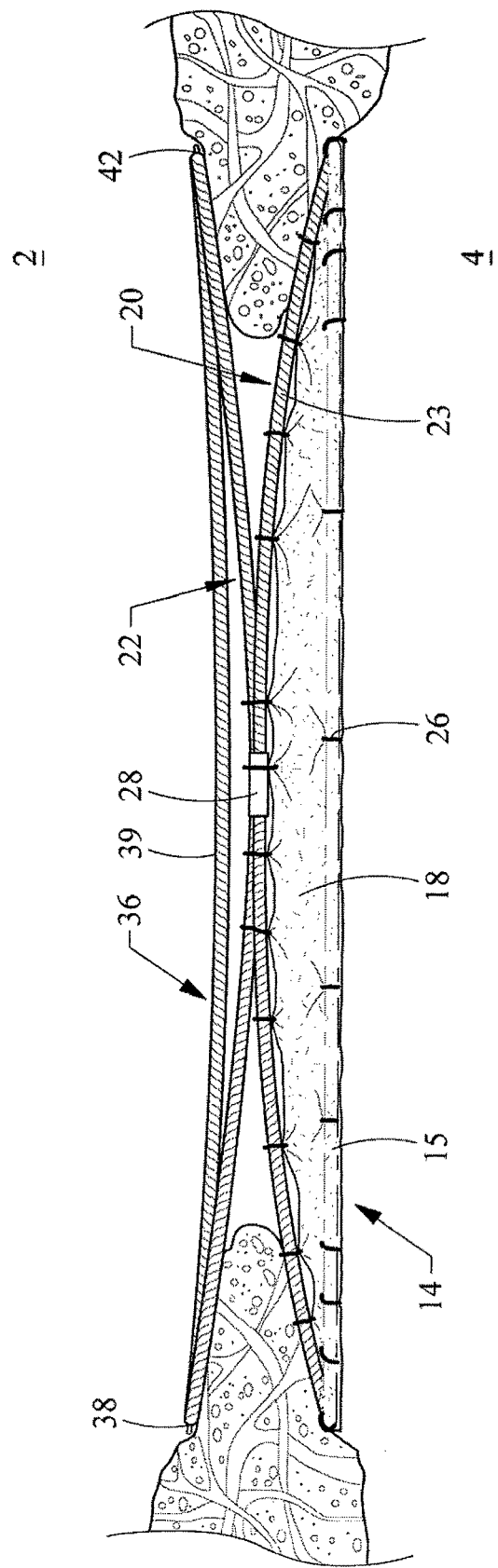
FIG. 5C illustrates a cross-sectional view illustrating the embodiment depicted in FIGS. 5A and 5B closing a PFO.

In a further aspect, one or more anchors 22 may include one or more anchor end pairs 38, 42, which are connected by a delivery bar 36 (FIGS. 5A-5B). A delivery bar 36 may be connected between the two opposite anchor ends in a single anchor device or it may connect two or more pairs of opposite anchor ends in a multiple anchor device (FIGS. 5A-5B). Anchor end pairs 38, 42 may be linked or unlinked to one another. Anchor end pairs 38, 42 are preferably linked when connecting two anchors to two crossbars 20.

A delivery bar 36 has a flexible, substantially linear structure configured to provide an alternative grasping member 34 for releasable attachment to a delivery release member 58. When attached to a suitable delivery release member 58 during delivery of the device, the delivery bar 36 can remain attached to the anchors 22 even after the anchors 22 have retracted against tissues during placement. In the event that the device 10 is found to be not properly positioned, anchorage of the delivery bar 36 to the delivery release member 58 permits the device to be easily withdrawn and/or repositioned as necessary.

Crossbars 20 and delivery bars 36 may be formed as flexible, substantially linear structures that may be configured from, or configured to include, a substantially one-dimensional tube, coil, bar, or wire having a circular, elliptical or polygonal cross-sectional shape. A crossbar 20 or delivery bar 36 is preferably hollow in nature. This can facilitate linkage to other device components using wires 16, for example. It should be noted, however, that any materials providing flexibility and interconnectivity can be used in place of a crossbar, including shape memory materials, braided wires and the like.

In the exemplary embodiments depicted in FIGS. 4 and 5, the frame 14 includes one or more flexible linear structures in the form of one or more linear frame coils 15 circularized into the shape of an ellipse or ring and connected to one crossbar 20 (FIGS. 4A-4B) or two crossbars 20 (FIGS. 5A-5E), each anchor being connected to a corresponding anchor 22. In one embodiment, a single frame coil 15 may be circularized to form a ring coil frame 14. In another embodiment, two frame coils 15 may be circularized to form a ring, each frame coil 15 defining a hemispheric coil ring portion.

FIGS. 4A and 4B exemplify an embodiment in which the crossbar 20 includes a crossbar coil 23, which is connected to the frame 14 or frame coil 15 by a wire 16. One or more wires 16 may be used to directly or indirectly connect a frame coil 15 to one or more crossbar coils. In FIGS. 4A and 4B the crossbar coil 23 is further connected to an anchor 22, more particularly an anchor coil 30 by a wire 16. One or more wires 16 may be used to interconnect the frame coil 15, crossbar coils 23, and anchor coils 30.

FIGS. 5A-5E exemplify embodiments in which the frame 14 is connected to two crossbars 20. A coupling member 28 is used to connect each crossbar 20, including a crossbar coil 23, to a different anchor 22, more particularly a different anchor coil 30.

In one embodiment, the coupling member 28 is formed from a small hollow cannula or band co-encircling the crossbar 20 and anchor 22. The coupling member 28 may be formed from any material suitable for coupling or joining a crossbar 20 to an anchor 22. A coupling member 28 may be used for linking any flexible linear structures according to the present invention. The coupling member 28 is preferably formed from a metallic material suitable for joining device components of the present invention, including but not limited to platinum, stainless steel, and nitinol.

Figure 5D:
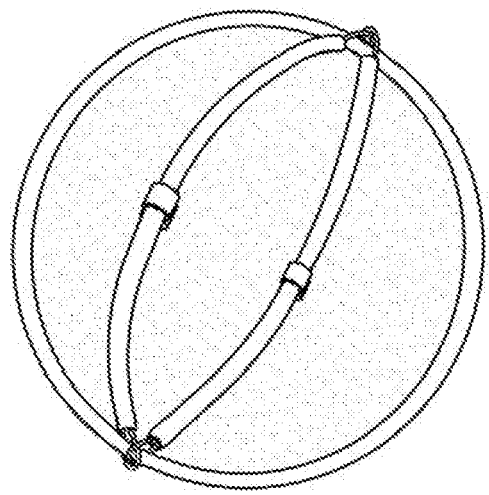
FIG. 5D is a photograph of an exemplary closure device according to FIG. 5A showing the side of the device facing away from the bodily opening when deployed.

Anchors 22 and delivery bars 36 may be further connected to one another by wires 16, by interlocking loop structures (for example, 34a, 34b) disposed at the terminal ends of the anchors 22 and the delivery bar 36, combinations thereof. In FIGS. 5A-5E, wires 16 are used to connect the crossbar coils 23 to the frame coils 15 and to connect the delivery bar coil 39 to the two anchors 22 (or anchor coils 30). FIG. 6A is a photograph showing the structural backbone corresponding to the design in FIGS. 5A-5E (without showing the attached sheet of biocompatible material) to illustrate a terminally disposed delivery bar loop structure 37 interlinking terminally disposed loop structures 34b1, 34b2 at the ends of the anchors 22. Thus, as an alternative to mediating releasable attachment to the delivery release member 58 when used in the context of the above described terminally disposed grasping members 34a, 34b, loop structures disposed at the terminal ends of the crossbars 20, anchors 22, and/or delivery bars 36 may be interlocked with one another to facilitate connectivity and enhanced swivelability therebetween. The closed loops can be formed, for example, from wires extending longitudinally through hollow structures, including coils, as described above. The enhanced swivelability conferred through the use of the interconnected loops can further provide enhanced collapsibility and expandability and can help to better conform the device to the architectural nuances unique to a given bodily passageway.

Figure 6A:
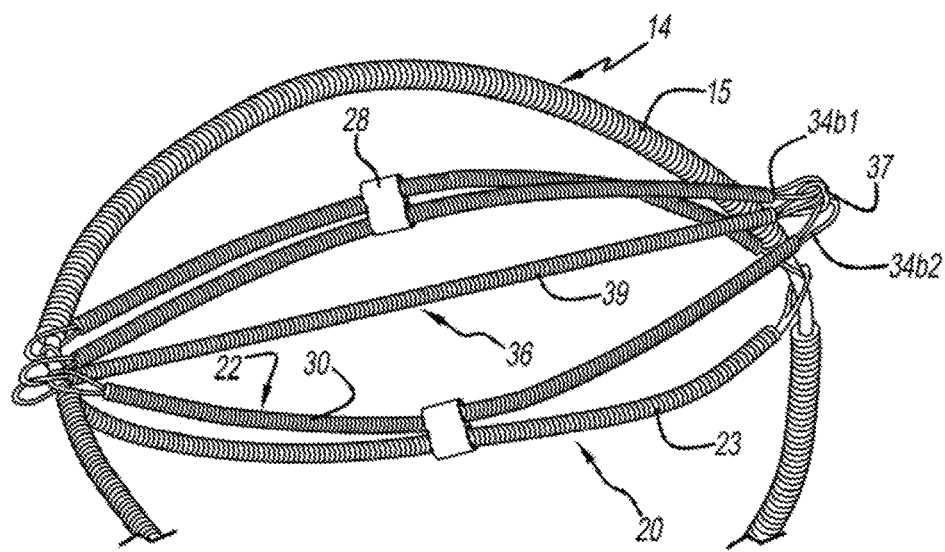
FIG. 6A illustrates the structural backbone of the device exemplified in FIGS. 5A-5E illustrating an aspect of the present invention.
Figure 6B:
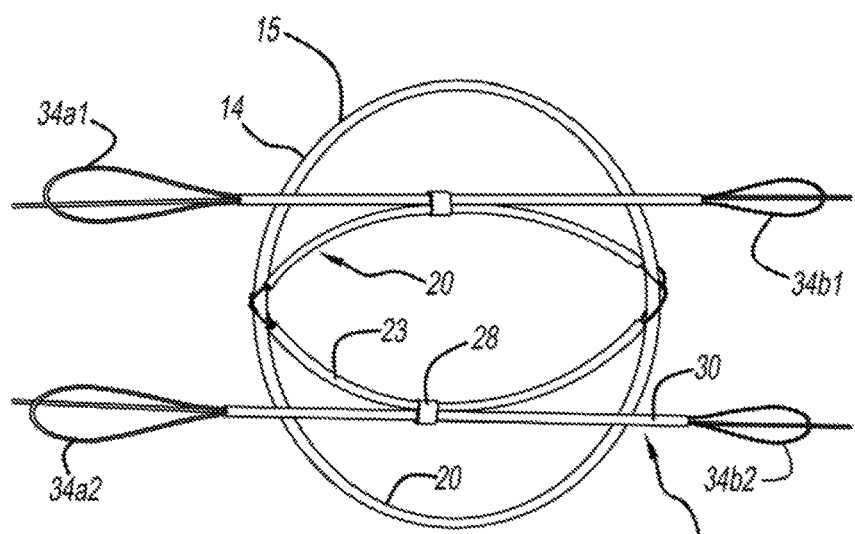
FIG. 6B illustrates the structural backbone of an exemplary closure device according to another embodiment of the present invention.

Although the above two crossbar, two anchor designs are described in the context of a delivery bar 36, similar devices can be employed without a delivery bar 36. For example, in an alternative embodiment, a closure device 10 may include two crossbars 20, including two crossbar coils 23 connected by a coupling member 28 to two anchors having terminally disposed grasping members 34a1, 34a2, 34b1, 34b2, whereby the anchors 22 are not linked to a delivery bar 36. In this case, the grasping members 34a1, 34a2, 34b1, 34b2 can directly mediate releasable attachment to a suitable delivery release member 58 as described above. FIG. 6B is a photograph illustrating a structural backbone exemplifying such a design (without showing the attached sheet of biocompatible material). In this case, the size of the terminally disposed loops can be adjusted by pulling on the free wire ends from the opposite side as described above.

In the closure devices of the present invention, one or more wires 16 may be used for interconnecting the frame 15, crossbars 20, anchors 22, and/or delivery bars 36. In addition to wires 16 and coupling members 28, the above described structural components may be connected to one another using any suitable attachment means known to those of skill in the art, including but not limited to the sutures, adhesives, soldering, welding, crimping, and the like.

FIGS. 4 and 5 exemplify closure devices 10 having a plurality of connected coils (or tubular members) 15, 23, 30, 39 connected by one or more wires 16. Any one of the frame 14, frame coil 15, crossbar 20, crossbar coil 23, anchor 22, anchor coil 30, delivery bar coil 39, or hollow tubular members thereof may be independently linked to one or more wires or they may be interlinked to other device components by one or more wires 16 or loop structures (for example, 34a, 34b) in one or more additional steps.

Accordingly, as shown in the embodiment depicted in FIGS. 5A-5E, a closure device 10 may include two crossbar coils 23 connected to a frame coil 15 by wires 16, and may further include a pair of anchor coils 30 connected to a delivery bar by wires 16. Use of any of the above described attachment means may be employed to directly or indirectly connect a frame 14 to the crossbars 20, anchors 22, and/or delivery bars.

To facilitate the joining of one or more crossbar coils 23 to any one of the frame coils 15 or anchor coils 30, or to facilitate the joining of any coiled structures of the present invention to the sheet 18 of biocompatible or bioremodelable material, any one of the various coiled structures may be partially stretched to create interrupted regions or open grooves to facilitate linkage between coils and/or biocompatible materials using for example, wires 16 or sutures 26. For example, as depicted in FIGS. 4A and 4B, open area crossbar coil grooves 25 may facilitate linkages between a crossbar 20 and an anchor 22 by providing open area connections to facilitate wire exchanges between the crossbar coil grooves 25 and anchor coil grooves 27. Open area coil grooves 25, 27 may also provide open area connections facilitating suture exchanges between a crossbar coil 23 or anchor coil 30 and a sheet 18 of biocompatible material.

In FIGS. 4A and 4B, a single wire 16 may be used to link a frame 14, crossbar 20, and anchor 22. More particularly, a single wire 16 may be used to circularize the linear frame coil 15, connectively link the circularized frame coil 15 to a crossbar coil 23, connectively link the crossbar coil 23 to an anchor coil 30, and form loop structures or grasping members 34, which are frictionally engaged by the anchor coil 30 at each end.

For example, a single wire 16 may be run through the frame coil 15 (or hollow, tubular frame 14) one or more times, at which point free wire ends at opposite ends of the frame 14 are run toward each other, through the crossbar coil 23 in opposite directions. After reaching the frame coil 15 end in each case, the crossbar coil 23 may be placed next to an anchor coil 30 in a parallel-spaced arrangement, whereby free wire ends 16a, 16b are exchanged from the crossbar coil 23 into internal anchor coil 30 portions carrying open stretched areas. The wire ends 16a, 16b may then be extended through the anchor coil 30 toward opposite ends in each case, looped back into the anchor coil 30, and extended across the full length of the anchor coil, whereby the excess free ends 16a, 16b can be clipped or further stabilized as necessary. By passing an appropriate length of wire 16 with sufficient slack, terminally disposed grasping members 34 or loop structures may be created at each anchor coil end 38, 42, which are frictionally engaged by the anchor coil 30.

Alternative wiring configurations for linking the frame 14, crossbar 20, and anchor 22 may be employed. For example, rather than using two wire ends 16a, 16b to interconnect the frame 14, crossbar 20 and anchor 22 (as in the previous example), a single wire end may be extended through one or more of these components for purposes of connection. Moreover, wire ends may be completely extended through the crossbar coil 23 and looped around the frame 14 before their exchange into the anchor coil 30. Additionally, one or more separately wired frames 14, crossbars 20 or anchors 22 may be connected to one another in successive steps.

As shown in FIG. 4B, portions of the crossbar 20 and anchor 22 may be connected at a region 32 designed for attachment to the sheet of biocompatible or bioremodelable material. An appropriate attachment region 32 may be provided by exchanging free wire ends 16a, 16b approaching one another from opposite directions through the crossbar coil 23 toward internal anchor coil 30 positions designated as 44a and 44b. The exchange points serve to define the outer boundaries of a preferred attachment region 32 for attaching the sheet 18 of biocompatible or bioremodelable material to the crossbar 20, anchor 22, or both, when using a crossbar 20. The attachment region 32 may be defined by a gap distance, d, in this case, between the two wire exchange points designated by 44a and 44b. As described above, the attachment region 32 may help to define the configuration of sheet material when deployed.

Sutures 26 may be used to securely link the sheet 18 of biocompatible or bioremodelable material over the attachment region 32 to the crossbar 20, anchor 22, or both. Although not essential, portions of the crossbar coil 23 and anchor coil 30 may be partially stretched as described above to create small open area grooves or gaps, which can serve to enhance the engagement between sutures 26 and coils 23, 30, and to facilitate wire transfer between the coils 23, 30 as shown in FIGS. 4A and 4B.

In some embodiments, a gap distance of about 8 to about 9 mm in an attachment region 32 was found to allow good self-centering, anchoring, and immediate closure for a variety of passageway sizes, including small (2-4 mm), medium (5-8 mm) and large (9-13 mm) bodily passageways, including those found in PFOs.

Depending on the nature and architecture of the bodily passageway slated for closure, and the presence and/or number of crossbars 20 employed in the device 10, several biocompatible material attachment region 32 options may be employed. Thus, in addition to being attached to the frame 14, the sheet 18 of biocompatible material may be additionally attached along at least a portion of at least one crossbar or along the length of the crossbar in its entirety. Alternatively, the sheet 18 of biocompatible material may be attached to frame 14 only.

For example, FIG. 5A illustrates a sheet 18 of biocompatible material being sutured to the frame 14, and to stretches of the crossbar, as well as a small stretch around the anchor surrounding the coupling member 28. FIG. 5B is a side view illustrating a modification to the device depicted in FIG. 5A whereby the biocompatible material is sutured along the entire length of the crossbar, in addition to the frame 14. Similarly, FIG. 5D is a photograph showing a sheet 18 of small intestinal submucosal (SIS) material sutured around the entire perimeter of the frame 14 and along the entire stretch of both crossbars 20.

A closure device 10 of the present invention is made of flexible materials so that the closure device is sufficiently collapsible to be retained and delivered from a variety of catheter delivery sizes, including 6-10 French size, preferably 6-8 French size. Accordingly, one or more of the component device parts of the closure device 10 may be made from flexible, radiopaque, materials such as platinum and/or or shape memory alloy materials, such as Nitinol, including those described in U.S. Pat. Nos. 4,665,906, 5,108,420, the disclosures of which are incorporated by reference herein.

Shape-memory materials may be included in a number of component device 10 parts, including, but not limited to the frame 14, anchor 22, anchor coil 30, grasping member 34, and anchor wires 46. The shape-memory materials, including Nitinol alloys, may be utilized whereby the alloy materials are compressed or partially expanded in its martensitic state and fully expanded in its austenitic state. A specific shape memory alloy may be chosen so that the frame 14 is in the austenitic state at body temperature. Prior to insertion into the body, the frame 14 may be maintained at a low temperature within the martensitic range. Upon delivery to a desired bodily location, the frame 14 may be warmed to at least the $A_f$ temperature so that it can expand to its desired configuration.

Suitable shape-memory materials and their use in medical applications is disclosed in U.S. Pat. No. 3,012,882 to Muldawer et al.; U.S. Pat. No. 3,174,851 to Buechler et al.; U.S. Pat. No. 4,665,906 to Jervis; U.S. Pat. No. 5,108,420 to Marks; U.S. Pat. No. 5,769,796 to Palermo et al., U.S. Pat. No. 5,846,247 to Unsworth et al.; and U.S. Pat. No. 6,451, 052 to Burmeister et al., the disclosures of which are expressly incorporated herein by reference.

Preferably, the frame 14 is made from, or includes, flexible radiopaque materials, and/or shape memory alloy materials. In a preferred embodiment, the frame 14 is made of platinum or Nitinol. Preferably, the wires 16, 46 used for linking components of the above-described closure device 10 include or are made from a suitable shape memory alloy materials. In a preferred embodiment, wires are used which are made from a Nitinol alloy.

Radiopaque marker materials may be used in the device components directly or they may be added to one or more components of the closure device 10 or assembly 40 so as to render them radiopaque or MRI compatible. In particular, radiopaque materials, fillers, metallic marker bands or powders may be included into one or more of the frame 14, wire 16, sheet 18, crossbar 20, crossbar coil 23, anchor 22, anchor coil 30, grasping member 34, anchor wire 46, or delivery catheter 54 to facilitate radiographic visualization of the device during the implantation process. Preferably, one or more of the frame coil 15, crossbar coil 23, anchor coil 30, and/or delivery bar coil 39 is made from or includes a radiopaque material (such as platinum) to facilitate radiographic visualization.

Exemplary radiopaque marker materials include but are not limited to, platinum, gold, tungsten, tantalum, tantalum powder, bismuth, bismuth oxychloride, barium, barium sulphate, iodine and the like. Metallic bands of stainless steel, tantalum, platinum, gold, or other suitable materials, can include a dimple pattern, which can further facilitate ultrasound or X-ray identification.

Radiopaque markers may be introduced in any form suitable for the rendering the closure device radiopaque or MRI compatible. In addition, the radiopaque materials can be incorporated in the closure device or assembly components by a variety of common methods, such as adhesive bonding, lamination between two material layers, vapor deposition, and the materials and methods described in U.S. Pat. Appl. Publ. No. 2003/0206860, the disclosure of which is incorporated herein by reference.

Sutures 26 for linking elements of the closure device 10 to one another may be made from a variety of suture types, including braided or monofilament. Sutures 26 may be made from polyester, polypropylene, polyglycolic acid, polytetrafluoroethylene (PTFE), SIS, nylon, silk or any of a variety of absorbable or nonabsorbable suture materials known in the art. The sutures 26 may be treated or coated with radiopaque materials to facilitate visualization of the device by radiography or fluoroscopy. The sutures 26 may also be coated with antibiotics or other antimicrobial agents. Exemplary suture materials include TEVDEK II®, a braided polyester suture material impregnated with PTFE; DEKLENE II®, a polypropylene monofilament suture material, and nylon monofilament suture material, all of which are manufactured by Genzyme Biosurgery of Cambridge, Mass. Preferred suture materials include non-absorbable polypropylene sutures, such as PROLENE™ 6-0 mil (0.1524 mm) diameter (Ethicon Inc., Piscataway, N.J.).

As an alternative to sutures 26, tissue adhesives may be used to link elements of the above disclosed closure device 10 to one another, such as the sheet 18 biocompatible sheet material to the frame 14. An exemplary tissue adhesive is BioGlue®) (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). MedPro Month (1999) 9:261-262; and MedPro Month (2000) 10:86-91.

Bioremodelable Sheet Materials

The closure device may include a sheet of bioremodelable material suitably configured to close a bodily passageway. The sheet of bioremodelable material is designed to promote angiogenesis and endothelialization of the implanted closure device. In particular, the bioremodelable material is capable of remodeling the surrounding tissues, such that upon implantation in a patient, the sheet of bioremodelable material is degraded and replaced by the patient's endogenous tissues. As the sheet of bioremodelable material is remodeled by host tissues, the bodily opening becomes stably closed, obviating concerns about migration of the device.

The sheet of bioremodelable material may include one or more bioremodelable tissue layers formed into a sheet. The sheet may include, for example, a single tissue layer containing ECM material, or it may include additionally adjacent tissue layers or additional tissue layers laminated together in a multilaminate structure. The sheet may include or be made from reconstituted or naturally-derived collagenous materials. Preferred bioremodelable materials include naturally derived tissues with ECMs possessing biotropic properties, including in certain forms angiogenic collagenous ECMs. Preferred ECMs include naturally-derived collagenous tissue materials retaining native matrix configurations and bioactive agents, such as growth factors, which serve to facilitate tissue remodeling, as opposed to collagen-based materials formed by separately purifying natural collagen and other associated components away from their native three dimensional matrix configurations or bioactive agents, including growth factors. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa tissue materials for these purposes include, for instance, intestinal submucosa, including small intestinal submucosa, stomach submucosa, urinary bladder submucosa, and uterine submucosa. A particularly preferred ECM material is porcine SIS material. Commercially available ECM materials capable of remodeling to the qualities of its host when implanted in human soft tissues include porcine SIS material (Surgisis® and Oasis® lines of SIS materials, Cook Biotech Inc., West Lafayette, Ind.) and bovine pericardium (Peri-Strips®, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), platelet derived growth factor (PDGF), and other growth factors known to those of skill in the art. As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein expression, gene expression, or combinations thereof.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances. Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable materials, including ECMs according to the present invention, may be isolated and used in the form of intact natural sheets, tissue layers, or strips, which may be optimally configured from a native, wet, fluidized, or dry formulation or states, into sheets, knitted meshes, or porous scaffolds, using one or more of the following, including stretching, chemical crosslinking, lamination under dehydrating conditions, compression under dehydrating conditions, in accordance with teachings set forth in U.S. Pat. Nos. 6,206,931 and 6,358,284; U.S. Patent Application Publication Nos. 2006/0201996, 2006/0052816, 200510249772, and 2004/0166169, the disclosures of which are expressly incorporated by reference herein.

In addition, bioremodelable materials according to the present invention may be treated by controlled autolysis to render the materials substantially acellular and less susceptible to post-implantation mineralization as described in U.S. Pat. Nos. 5,595,571, 5,720,777, 5,843,180, 5,843,181, and U.S. Patent Application Publication Nos. 2005/020612, the disclosures of which are expressly incorporated by reference herein.

Other Biocompatible Sheet Materials

Bioremodelable sheet materials provide a preferred source of biocompatible sheet materials for attachment to the frame. However, other biocompatible sheet materials may be used in place of bioremodelable sheet material, including composites thereof. Biocompatible sheet materials include a variety of natural or synthetic polymeric material known to those of skill in the art which can be formed into a flexible sheet material covering the above described frame. Exemplary biocompatible sheet materials include polymeric materials; fibrous materials; thrombogenic fibrous materials, and other materials known to those of skill in the art.

Biocompatible sheet materials may be formed from fibers, or any suitable material (natural, synthetic, or combination thereof) that is pliable, strong, resilient, elastic, and flexible. The material should be biocompatible or capable of being rendered biocompatible by coating, chemical treatment, or the like. Thus, in general, the material may comprise a synthetic biocompatible material that may include, for example, bioresorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof; polyurethanes, including THORALON™ (THORATEC, Pleasanton, Calif.), as described in U.S. Pat. Nos. 4,675,361, 6,939,377, and U.S. Patent Application Publication No. 2006/0052816, the disclosures of which are incorporated by reference herein; cellulose acetate, cellulose nitrate, silicone, polyethylene teraphthalate, polyamide, polyester, polyorthoester, polyanhydride, polyether sulfone, polycarbonate, polypropylene, high molecular weight polyethylene, polytetrafluoroethylene, or mixtures or copolymers thereof, a polyanhydride, polycaprolactone, polyhydroxy-butyrate valerate, polyhydroxyalkanoate, or another polymer able to be made biocompatible.

Thrombogenic fibrous materials include synthetic or natural fibrous material having thrombogenic properties. Exemplary thrombogenic fibrous materials include, but are not limited to, DACRON, cotton, silk, wool, polyester thread and the like.

The polymeric materials may include a textile material. The textile includes fibers and may take many forms, including woven (including knitted) and non-woven. Preferably, the fibers of the textile comprise a synthetic polymer. Preferred textiles include those formed from polyethylene terephthalate, polytetrafluoroethylene (PTFE), expanded polytetrafluoroethylene (ePTFE), and PTFE. These materials are inexpensive, easy to handle, have good physical characteristics and are suitable for clinical application. These materials may be attached to or rolled around a hollow tube or coil as described above.

Examples of biocompatible materials from which textiles can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material, provided the final textile is biocompatible. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. More preferably, the textile is made of a biocompatible polyester. Examples of biocompatible polyesters include DACRON (DUPONT, Wilmington, Del.) and TWILLWEAVE MICREL (VASCUTEK, Renfrewshire, Scotland).

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON" when manufactured by DuPont), and by other companies from various substances.

Non-native bioactive components, such as those synthetically produced by recombinant technology or other methods, may be incorporated into these other biocompatible materials. These non-native bioactive components may be naturally-derived or recombinantly produced proteins, such as growth factors, which are normally found in ECM tissues. These proteins may be obtained from or engineered from any animal species. The non-native bioactive components may also be drug substances. Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the biocompatible material as a premanufactured step, immediately prior to the procedure (for example, by soaking the material in a solution containing a suitable antibiotic such as cefazolin), or during or after engraftment of the material in the patient.

Closure Device Assembly

In a further aspect, a closure assembly for delivering a closure device according to the present invention is provided. The closure device assembly includes a delivery catheter, a delivery release member, and a collapsibly disposed closure device. The delivery release member includes one or more structural portions for releasable attachment to at least one anchor or delivery bar in the closure device. In a further aspect, the delivery release member is preferably positioned in a locking catheter preventing inadvertent release of the closure device when held in a compressed state inside the delivery catheter The delivery release member may include an anchor engaging portion or a delivery bar engaging portion, including at least one structure selected from the group consisting of hook, ball, loop, cup, jaw or combination thereof. Upon disengagement of an anchor grasping member or delivery bar from the delivery release member, for example, the covered frame 14 of sheet material 18 can be released so as to cover an opening of the bodily passageway, whereby one or more anchors 22 are secured to the opposite end of the bodily passageway, thereby sandwiching the device 10 around and through a bodily passageway, such as a PFO.

In one embodiment, the delivery release member includes a complementary structure (including for example, biopsy jaws or cups) to facilitate releasable linkage to at least one grasping member 34 in the anchor 22, such as a wired loop 34a, 34b. One or more grasping members 34 may be terminally disposed on the one or more anchors 22. As described above, each anchor 22 may be formed from an anchor coil 30 having an anchor wire 46 extending longitudinally therethrough. The anchor wire 46 may be configured to include at least one terminally disposed grasping member 34a, 34b frictionally engaged by the anchor coil 30.

In another embodiment, the delivery release member includes a complementary structure, such as a hook, to facilitate releasable linkage to a flexible delivery bar connected between one or more pairs of anchor ends as shown in FIGS. 5A-5E. Use of hook release system is similarly adaptable to delivery of the closure devices 10 described herein by way of the terminally disposed grasping members 34.

Figure 7A:
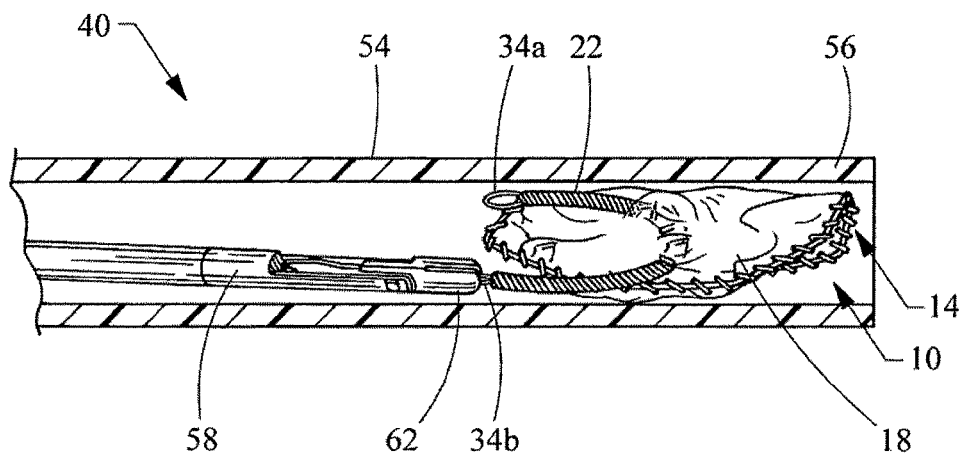
FIG. 7A illustrates a closure device assembly according to an embodiment of the present invention.
Figure 7B:
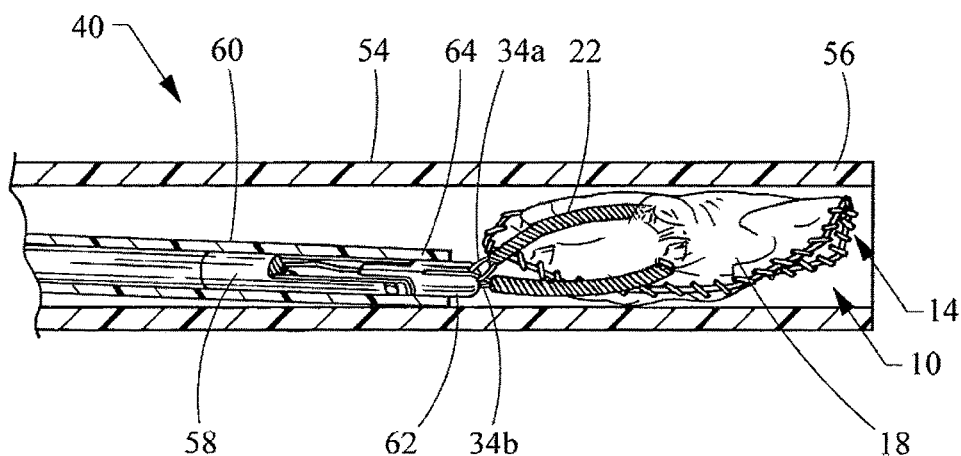
FIG. 7B illustrates a closure device assembly according to another embodiment of the present invention.

FIGS. 7A and 7B depict exemplary closure device assemblies 40 facilitating rapid deployment of the closure device 10. These closure device assemblies include a delivery catheter 54 containing a preloaded, collapsibly disposed closure device 10 disposed near the distal tip of a delivery catheter 54. The assemblies 40 further include an anchor release member 58 depicted as a biopsy forceps securely linked to one (FIG. 7A) or more (FIG. 7B) terminally disposed grasping members 34 in the anchor 22 of the closure device 10. These linkages facilitate positioning and uncoupling of the closure device 10 from the delivery catheter 54 in connection with closure device 10 deployment. FIG. 7A depicts an anchor release member as a biopsy forceps 58 linked to a single loop structure 34; FIG. 7B depicts a linkage between biopsy forceps 58 and two loop structures 34 terminally disposed in the anchor 22.

FIG. 7B further depicts an additional safety feature preventing premature disengagement of the closure device 10 from one or more anchors 22 prior to or during release of some or all of the device 10 from the delivery catheter 54. In particular, the delivery catheter 54 further includes a biopsy forceps 58 which is passed through a smaller, coaxially positioned locking catheter 60. The biopsy cups 62 of the biopsy forceps 58 are connected to two terminally disposed loop structures 34a, 34b in the anchor 22. The locking catheter 60 and the biopsy forceps 58 are configured so that the biopsy cups (or jaws) 62 are prevented from inadvertently releasing the closure device 10 while positioned inside the delivery catheter 54. In particular, the distal end of the locking catheter sheath 64 overhangs at least a portion of the biopsy cups (or jaws) 62, thereby preventing premature disengagement from anchors 22 in the tip-pre-loaded closure device 10 from the biopsy forceps 58 prior to or during release of some or all of the device 10 from the delivery catheter 54.

In one embodiment, the anchor release member 58 comprises biopsy forceps containing anchor engaging portions in the form of jaws or cups 62. Suitable biopsy forceps for use in the present invention include Cup Biopsy Forceps (Cook Urological, Inc., Spencer, Ind.) and Biopsy Cup Forceps (ACMI Corp., Southborough, Mass.).

Figure 7C:
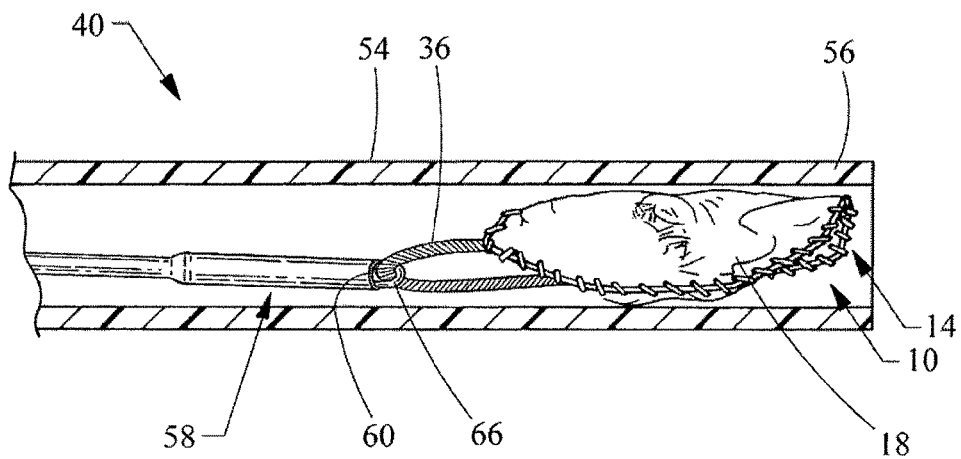
FIG. 7C illustrates a closure device assembly according to another embodiment of the present invention.

FIG. 7C depicts an exemplary closure device assembly 40, including a preloaded, collapsibly disposed closure device 10 depicted in FIGS. 5A-5E. The depicted assembly 40 includes collapsibly disposed closure device 10 disposed near the distal tip of a delivery catheter 54. In FIG. 7C, the assembly 40 includes a delivery catheter 54 housing a delivery bar release member 58 in the form of a smaller, coaxially positioned locking catheter 60 connected to a hook 66 that is subject to a spring tension release mechanism. The linkage between the hook 66 and the delivery bar 36 can facilitate accurate placement and uncoupling of the closure device 10 from the delivery catheter 54 in connection with closure device 10 deployment.

As depicted in FIG. 7C, the distal end of the locking catheter 60 includes a hollow cannula 64 overhanging at least a portion of the hook 66, whereby the spring tension release mechanism prevents premature disengagement of the delivery bar 36 from the hook in the tip-preloaded closure device 10 or following retraction of the delivery catheter 56 or following extension of the locking catheter 60 out of the delivery catheter 54 during delivery of the device.

In one embodiment, the Gunther Tulip™ Vena Cava filter delivery system (Cook Inc., Bloomington, Ind.) provides an exemplary locking catheter 60 (a metal cannula in this case) for releasable attachment and delivery of closure devices 10, including those configured to include a delivery bar 36 as described above. Components in the Gunther Tulip Vena Cava filter delivery system, including the hook, delivery sheath, or locking catheter, can be shape-modified or size-modified to accommodate a variety of closure device sizes or grasping members, including delivery bars 36 and one or more terminally disposed loop structures 34 at the end of one or more anchors.

Figure 8A:
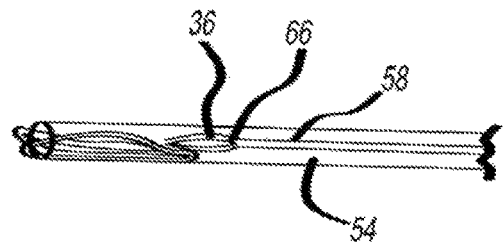
FIG. 8A is a photograph of the device assembly represented in FIG. 7C.
Figure 8B:
FIGS. 8B and 8C are photographs showing the distal end of the closure device assembly exemplified by FIG. 8A illustrating the releasable unfolding of an anchored covered ring frame.
Figure 8C:
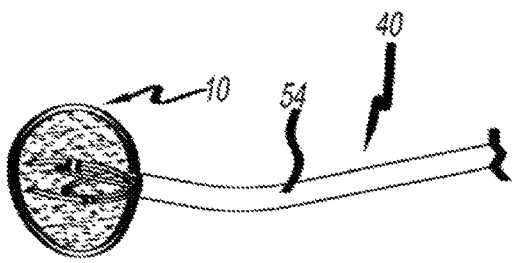
Figure 8D:
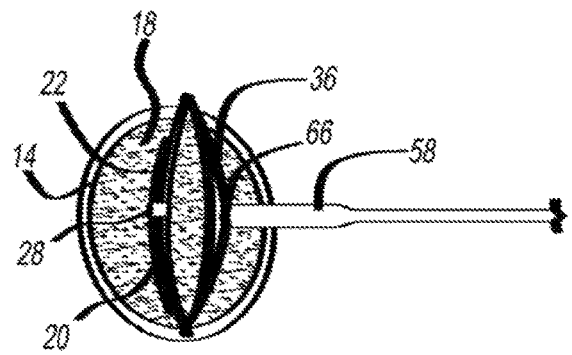
FIG. 8D is a photograph showing an exemplary locking catheter showing attachment of a delivery bar to a delivery member.

FIG. 8A is a photograph of a device assembly, including a transparent catheter sheath exemplifying the assembly represented in FIG. 7C, including the coaxially positioned locking catheter 60 hooked to a delivery bar 36. FIGS. 8B and 8C are photographs showing the distal end of the closure device assembly exemplified by FIG. 8A to illustrate the releasable unfolding of an anchored covered ring frame device 10. FIG. 8D is a photograph showing an exemplary locking catheter 60 showing attachment of the delivery bar 36 to the delivery bar release member 58.

As described above, the closure device 10 is made from sufficiently flexible materials to enable the device 10 to be collapsibly disposed in a relatively small delivery catheter 54 (including 6 to 8 French). The closure device may be preloaded at the tip of the delivery catheter 54 in an unexpanded, first configuration. When the closure device 10 is expelled from the delivery catheter 54, it may expand to a second, expanded configuration, particularly when the closure device 10 is made from shape memory materials. Non shape memory materials, such as stainless steel and the like, may be used for closure devices 10 requiring a lower degree of compression or expansion upon release.

In a preferred embodiment, the closure device assembly 40 includes a delivery catheter 54 with a curved flexor catheter sheath 56, and a collapsibly disposed closure device 10 preloaded at the sheath tip and connected to a biopsy forceps 58 held within a locking catheter. In a particularly preferred embodiment, the closure device assembly 40 includes a curved 6, 7, or 8 French delivery catheter; a 4 or 5 French locking catheter 60 holding the biopsy forceps 58; and a collapsibly disposed closure device 10. Flexor® Introducer Sets (Cook Medical Inc., Bloomington, Ind.) provide a preferred source of delivery catheters for use in the present invention.

The delivery catheter 54 may be configured for "long wire" or "over-the-wire" (OTW) delivery or for "short wire" or rapid exchange (RE) delivery procedures known to those of skill in the art. Accordingly, the delivery catheter 54 may be structurally modified with apertures or modified lumenal portions to allow exchange from the angioplasty wire guide to the delivery catheter 54 by RE without the need to replace the wire guide with an exchange-length guide wire before exchanging the catheters. Exemplary RE catheters that may be used to deliver the closure device 10 of the present invention are described in U.S. Pat. Nos. 5,690,642; 5,814,061; 6,371,961; and U.S. Pat. Application Nos. 2005/0070794; 2005/0125050; and 2005/0070821, the disclosures of which are expressly incorporated by reference herein.

To enhance the shelf life of the closure device containing bioremodelable materials, the device 10 may be lyophilized in an elongated form inside a cartridge sheath having a similar inner diameter sheath size as the delivery catheter 54 (for example, 6-8 French size). In view of their low device profile, closure devices 10 of the present invention can be delivered and securely deployed from a single, tip preloaded delivery catheter for immediate and complete passageway closure in as little as 15 minutes.

Method for Closing a Bodily Opening

In a further aspect, the present invention provides a method for closing or occluding a bodily opening in a patient using any of the above described closure devices 10 or closure device assemblies 40. In a preferred embodiment, a method for closing or occluding a septal opening, such as a PFO using a closure device assembly is provided herein.

By way of example, FIGS. 9A-9E depict an exemplary method for closing a PFO with an exemplary closure device assembly 40 depicted in FIG. 7B. In this example, multiple delivery components are included in the closure device assembly 40 to allow completion of the deployment process in as little as 10-15 minutes. The closure device assembly 40 includes a delivery catheter 54, an anchor release member depicted as a biopsy forceps 58 passed through a catheter 56, whereby a closure device 10 of the present invention is collapsibly disposed near the tip of the delivery catheter sheath 56. The closure device includes a circumferential frame 14 covered by a sheet 18 of bioremodelable material, which is directly attached to an anchor 22 containing a grasping member depicted as a wire loop structure 34 linked to a biopsy forceps 58.

Figure 9A:
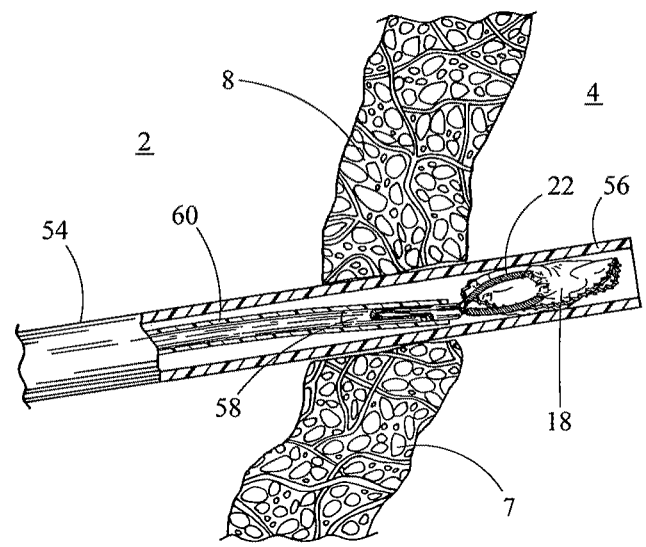
FIG. 9A illustrates a cross-sectional view of the distal end of the closure device assembly of FIG. 7B inserted and extending through a PFO.
Figure 9B:
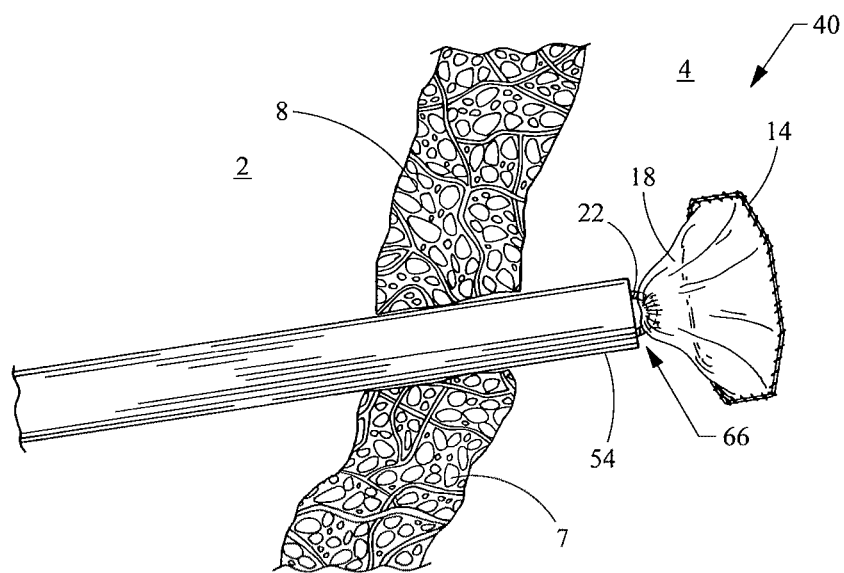
FIG. 9B illustrates a cross-sectional view of the distal end of the closure device assembly of FIG. 7B extending through a PFO and releasably unfolding an anchored sheet proximal to the distal side of the PFO opening.

An exemplary method for delivering any one of the above-described closure devices 10 includes passing a stiff guide wire through a suitable multi-purpose catheter and positioning the guide wire in the left atrium 4 across a bodily passageway, such as a PFO. In FIG. 9A, the delivery catheter 54 of the closure device assembly 40 has been introduced over the wire (not shown) and positioned into the left atrium 4 of a patient, through a bodily passageway, depicted here as a PFO 9 (FIG. 9A). Before releasing the device 10 or any part thereof, its position may be assessed by contrast media injection though the delivery catheter 54. Following confirmation of left atrium 4 positioning, the covered frame 14 is released from the delivery catheter 54 into the left atrium 4 proximate to the distal opening 66 of the PFO (FIG. 9B). This may be performed by retracting the delivery catheter sheath 56.

To prevent inadvertent release of the closure device 10 when held in a compressed state inside the delivery catheter 54, the anchor release member 58 (depicted here as biopsy forceps) may be positioned in a locking catheter 60. Once the sheath 64 of the locking catheter 60 is pulled back, the tips (or jaws) 62 of the biopsy forceps 58 can be released from grasping members 34 (depicted here as terminally disposed loop structures) in the anchor 22. In addition, the locking catheter may be used as a pusher to release the covered frame 14.

Following release of the covered frame 14 from the distal end of the delivery catheter 54, the delivery catheter 54 is retracted through the PFO passageway 9, pulling the covered frame 14 in toward the distal opening 66 of the PFO, and positioning the flexible anchor 22 at the distal end of the delivery catheter in the right atrium 2 near the proximal opening 70 of the PFO (FIG. 9C). Following proper confirmation of right atrium 2 device 10 positioning, the locking catheter sheath 64 may be pulled back to disengage the biopsy cups 62 in the biopsy forceps 58 from the terminally disposed loops 34 in the anchor 22, thereby releasing the anchor 22 into the right atrium 2 near the proximal opening 70 of the PFO (FIG. 9D). Alternatively, when a locking catheter is not used, the delivery catheter sheath 65 may be retracted to release the anchor 22 from the end of the delivery catheter 54.

The closure device 10 is self-expanding and retains its original shape following release. Upon release from the delivery catheter 54, the anchor 22 linearly expands, springing back against the septum primum 7 and septum secundum 8 on the proximal side of the PFO, and anchoring the frame 14 over the distal PFO opening. Consequently, the sheet covering 18 over the frame 14 can adapt to the size and shape of the PFO, filling in and occluding the PFO (FIG. 9E). The delivery catheter 54, locking catheter 60, and biopsy forceps 58 are then removed.

The above described method may be also applied to delivery of any other closure devices 10 of the present invention, including, for example, the device 10 exemplified in FIGS. 5, 6, and 8. In this case, release of the device 10 is predicated on the positioning and release of the device via a delivery bar 36 as described above.

Of course, any method for closing a bodily passageway, including PFOs, may be practiced using any of the above-described closure devices 10 or assemblies, and may therefore include a variety of biocompatible material-based sheet 18 coverings, in addition to bioremodelable materials or composites thereof, as well as a variety of materially different frames 14, crossbars 20, anchors 22, and delivery bars 36 as described above.

Preferably, the sheet 18 of biocompatible material attached to the frame 14 includes ECM- or submucosal tissue materials configured to stimulate angiogenesis and remodel portions of the bodily passageway, whereby the ECM or submucosal tissue is absorbed and replaced by host tissues so as to stably occlude the bodily passageway.

As an alternative to the pre-assembled over-the-wire assembly described above, one can alternatively introduce and position a wire guide through a suitable catheter or sheath near the site of the passageway opening; load the collapsible closure device 10 into the sheath; push the closure device 10 to the desired site with a biopsy forceps, pushing catheter or other suitable pushing device; and release the closure device 10 as described above.

Preferably, the deployed closure device 10 includes submucosal tissue that is configured to stimulate angiogenesis. In addition, the closure device 10 is preferably implanted so that the closure 10 occludes all or at least a portion of the bodily passageway, whereby the submucosal tissue is stably absorbed and replaced by host tissues.

As an alternative to the above method, the closure device 10 may be deployed whereby anchors 22 are released first, followed by the covered frame 14 analogously linked, in this case, to a delivery bar 36 or grasping members 34 disposed in the frame for attachment to a suitable delivery release member 58.

Visualization of the assembly 40 within the interior of the heart during deployment may be provided by various means. For example, fluoro-visible (or radio-opaque) dyes may be injected into the cardiac chambers and venous anatomy so that the chambers of the heart and the related vasculature are visible using a fluoroscopic device. This procedure, sometimes referred to as a venogram, allows the surgeon to locate a precise site and achieve proper device placement when performing an implant procedure.

Additionally, an ultrasonic probe may be positioned in the patient's esophagus, on the surface of the patient's chest, or in the chest cavity adjacent or in contact with the exterior of the heart to ultrasonically image the interior of the heart. In particular an intravascular ultrasound (IVUS) catheter may be utilized in conjunction with the above assembly 40 to provide ultrasonic imaging. Alternatively, an endoscope with a translucent bulb or balloon over its distal end may be introduced into the heart through the closure device assembly or through a separate incision in the wall of the heart to allow video-based or direct visualization of the interior of the heart. An angioscope introduced into the heart endovascularly through a peripheral vessel may also be used for intracardiac visualization. Fluoroscopy or magnetic resonance imaging (MRI) may provide an additional means for visualization.

Sheaths, dilators, catheters, multi-purpose catheters, pushing catheters, wire guides and needles used in the present invention can all be conventional marketed products or modifications thereof. For example, sheaths can be formed from PTFE (such as Teflon) or polyamide (such as Nylon) material, or a combination of materials such as an assembly including an inner layer of PTFE, a flat wire coil over the PTFE for kink resistance, and a polyamide (Nylon) outer layer to provide integrity to the overall structure and a smooth surface (as in the Flexor® Introducer Sets, Cook Medical Inc., Bloomington, Ind.). Dilators can be made from conventional dilator/catheter type materials such as polyethylene, polyamide, polyurethane or vinyl, or any combination of these materials. Fittings provided for sheath/dilator assemblies can be conventional elements such as luer locks; the dilator and the locking catheter can have fittings allowing them to be locked to the sheath during insertion and manipulation. Catheters can be made from conventional materials such as polyethylene, polyamide, PTFE, polyurethane, and other materials. Assembly components, including biopsy forceps may be separately contained in interlumenal sheaths within the delivery catheter or they may be disposed through secondary lumenal portions formed in the delivery catheter, as in double lumen catheters and the like.

The delivery catheter includes a sheath having a lumen diameter sized to allow for the introduction of the closure device to occlude the bodily passageway of interest. Illustratively, the inner diameter (I.D.) of the delivery sheath may range from 6 to 10 French or more, depending on the size of the closure device and the bodily passageway for closure. In preferred embodiments the delivery catheter includes an inner diameter of 6 to 8 French (corresponding to an I.D. between 0.087 inches, 0.100 inches, and 0.113 inches, respectively).

A closure device 10 or assembly 40 according to the present invention is particularly suited for closing septal heart defects, including PFOs and other atrial septal or ventricular septal defects. However, the closure device 10 can be similarly applied to closing or occluding a variety of other heart openings, tissue openings, vessels, vessel punctures, ducts, and other tissue openings where closure is desired.

Closure Device Repositioning or Removal

In some instances it may be necessary to reposition or remove the closure device, particularly when it includes sufficiently flexible materials or a sufficiently flexible structural configuration. This may occur where the device is not appropriately positioned or sized for a particular bodily passageway and/or fails to completely seal the passageway. In cases where it is necessary or advisable to reposition the closure device following initiation of deployment or prior to full deployment, a delivery release member may be used to reposition the device. In this case, a delivery release member remaining connectively linked to a delivery bar or one or more anchors may be pushed back into the side of the bodily passageway holding the covered frame and pulled back into the delivery sheath, at which point repositioning of the covered frame can be initiated prior to full deployment (and release) of the anchor.

In cases where it is necessary or advisable to remove the closure device following full deployment, a suitable foreign body retrieval device, such as a snare, may be used to remove the device. The snare may be delivered through the introducer sheath using a snare catheter. Preferred snares are commercially available under the trade names Needle's Eye® Snare (Cook Medical, Bloomington, Ind.) and Microvena Amplatz Goose Neck® Snare (ev3 Inc., Plymouth, Minn.). After positioning the snare around an anchor and advancing the anchor through the passageway where the covered frame is held, the device can be pulled back into a delivery catheter sheath and removed.

EXAMPLES

Example 1

To demonstrate the use of a closure device according to the present invention, experiments were conducted in both pigs and sheep using an octagon-shaped closure device exemplified in FIG. 2. In a particular example, a self-expanding octagon-shaped closure device was used to achieve immediate and complete closure of a PFO in a pig (swine #3959) using an over-the-wire delivery system. Deployment of the PFO device was completed in as little as 10-15 minutes.

Briefly, a right atrial venogram indicated a PFO 5-6 mm in diameter (FIG. 10A). A multipurpose catheter was used to place a stiff tip 0.035 inch coiled guide wire into the left atrium of the pig. A curved 8 French Flexor® sheath delivery catheter (Cook Medical Inc., Bloomington, Ind.; 0.113 inch inner lumen diameter) carrying a compressed, tip-preloaded SIS-covered octagon-shaped closure device with a single anchor was advanced over the guide wire into the left atrium (FIG. 10B). The guide wire was removed from left atrium and the octagon-shaped frame was released from the Flexor® sheath catheter into the left atrium. Upon release from the Flexor® sheath, the covered octagon-shaped frame expanded into its originally predetermined circumferential shape. At this point, the radiopaque anchor formed an oval shaped structure attached to biopsy forceps secured within a coaxially positioned 5 French locking catheter.

The delivery flexor catheter holding the 5 French catheter housing the biopsy forceps linked to the closure device was then retracted through the opening of the PFO and the covered frame was pulled against the septum primum and the septum secundum, positioning the flexible radiopaque anchor in the right atrium proximate to the proximal PFO opening (FIG. 10C). Before releasing the octagon-shaped closure device, its position was assessed by contrast media injection though the flexor sheath. The contrast media injection demonstrated complete closure of the PFO. At this point, the 5 French locking catheter was pulled back to expose the cups of the biopsy forceps and to disengage the anchor therefrom. Upon release, the anchor sprang back against the septum primum and the septum secundum, anchoring the closure device through the PFO passageway.

Figure 10F:
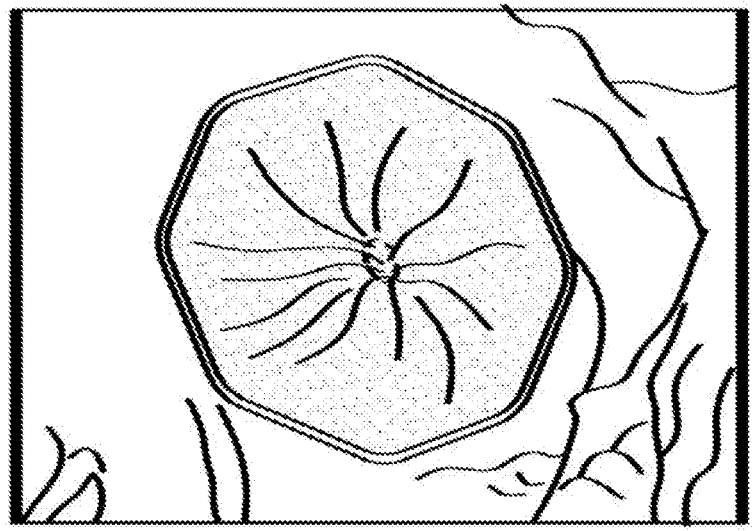
FIG. 10F is a photograph of an implanted closure device in a pig, illustrating deployment of the covered octagon frame in FIGS. 10A-10E on the distal side of a PFO in swine (swine #3959).
Figure 10G:
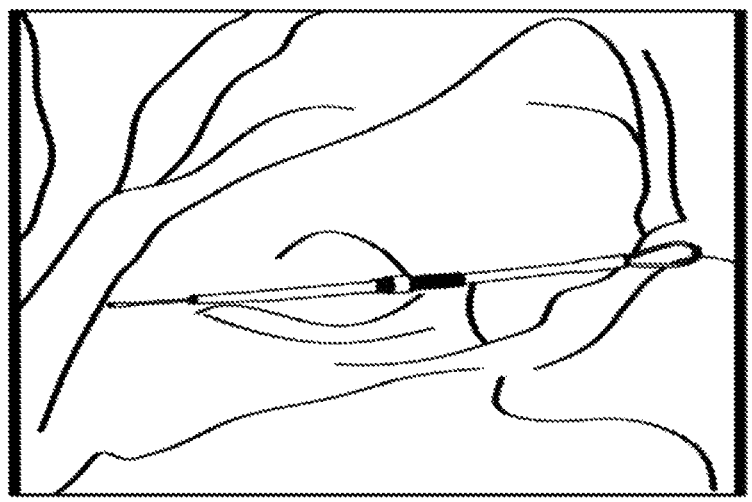
FIG. 10G is a photograph of the implanted closure device depicted in FIG. 10F, illustrating deployment of an anchor on the proximal side of the PFO.

Subtraction right atrial venography (in lateral view) showed complete, immediate closure of the PFO (FIG. 10D). A chest X-ray (in lateral view) depicted the radiopaque closure device after placement (FIG. 10E). Complete closure of the PFO as evidenced by follow-up subtraction right atrial venography 2 hours after implantation. FIG. 10F depicts the SIS-covered octagon portion of the device implanted on the distal side of the PFO in swine #3959. FIG. 10G depicts the implanted anchor in the proximal side of the PFO in swine #3959.

Example 2

Additional experiments in sheep demonstrated complete, immediate closure of a PFO in a lamb using a 7 French Flexor® sheath delivery catheter (Cook Medical Inc., Bloomington, Ind.; 0.100 inch inner lumen diameter) carrying a compressed, tip-preloaded octagon-shaped closure device containing two anchors attached to an SIS-covered octagon frame. A first anchor was held inside a 5 French locking catheter sheath. The second anchor was secured to a biopsy forceps held in the 5 French locking catheter by way of two terminally disposed loop structures. In this configuration, partial retraction of the 5 French sheath initially released a first anchor held in the lumen of the locking catheter. Further retraction of the 5 French sheath disengaged the biopsy forceps from the second anchor, releasing the closure device and anchoring the closure device through the PFO passageway.

Example 3

To evaluate closure of a bodily passageway and subsequent removal of the device after deployment, a closure device containing a crossbar and anchor connectively linked to a coiled ring device having a 17 mm diameter frame (as exemplified in FIG. 4) was tested in a young swine with an open PFO. Using a balloon catheter, the size of the PFO was measured as being 8 mm in diameter. By way of the right femoral vein, a soft tip guide wire was positioned through the PFO into the left atrium. Then, a delivery device assembly containing the coiled ring device preloaded at the tip of a curved 8 French Flexor® sheath delivery catheter (Cook Medical Inc., Bloomington, Ind.; 0.113 inch inner lumen diameter) and connectively linked to a biopsy forceps. The delivery device assembly was advanced over the guide wire into left atrium. The coiled ring was released near the distal PFO opening, and the assembly was retracted back through the PFO, pulling the ring up against the intra-atrial septum. Before releasing the device from the biopsy forceps, the device was repositioned twice using a biopsy forceps contained within a locking catheter. The anchor was then disengaged from the biopsy forceps. Contrast injection into the right atrium demonstrated immediate, complete closure of the PFO. Following a 6 hour observation period, the coiled ring device was removed using a Microvena snare for foreign body retrieval (ev3 Inc., Plymouth, Minn.). After positioning the snare around the anchor and advancing the anchor into the left atrium, the coiled ring device was pulled back into an 8 French Flexor® sheath and removed.

Example 4

A sheep atrial septal defects (ASD) model was tested to evaluate closure of a bodily passageway using a device embodiment exemplified in FIGS. 5 and 6. ASDs 9 mm and 11 mm in diameter were created using a percutaneous transeptal technique from right femoral vein. An angioplasty balloon was inflated within interatrial septum to enlarge the hole. An occlusion balloon (Boston Scientific) was used to further enlarge and then measure the size of ASD.

Figure 5E:
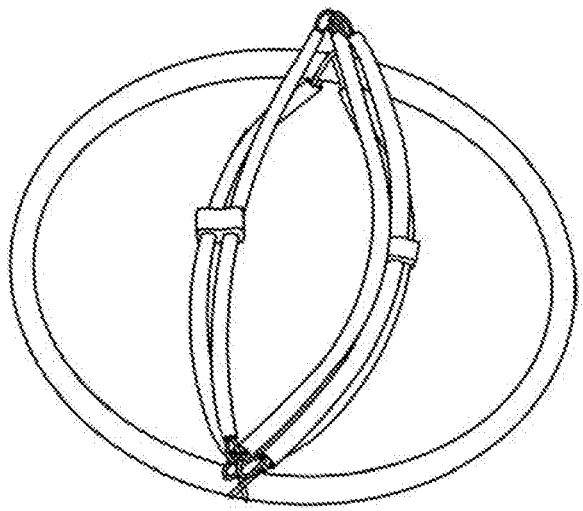
FIG. 5E is a photograph of the device depicted in FIG. 5D illustrating elements associated with anchoring and deployment.
Figure 11A:
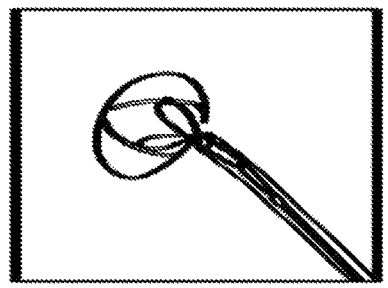
FIGS. 11A-11F are sequential venograms showing delivery and release of an SIS-covered ring frame from a compressed, tip-preloaded closure device exemplified in FIGS. 5D and 5E into the left atrium and positioning of the anchored assembly in the right atrium proximate to an interatrial septum created in a sheep (sheep #2017).
Figure 11D:
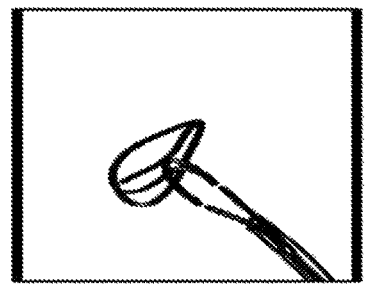
Figure 11B:
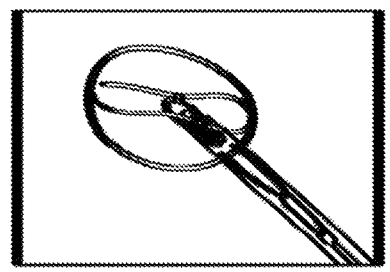

SIS-covered coiled ring closure devices according to FIGS. 5D and 5E containing two crossbars and two anchors (20 mm or 23 mm ring diameters) were implanted into two sheep (Sheep #s 2017 and 2016, respectively). Following ASD creation, a 9 Fr Flexor sheath containing a tip-preloaded SIS covered coiled ring attached to a hook-release locking catheter used in the Tulip filter delivery system (Cook, Inc.) was advanced across the ASD defect into left atrium. Following extrusion into the left atrium, the covered ring expanded from its collapsibly disposed state to facilitate ASD closure (FIG. 11A). Pulling the ring against the septum, the anchors and delivery bar were pulled back into the Flexor sheath to facilitate their deployment on the other side of the inter-atrial septum (FIG. 11B).

Figure 11E:
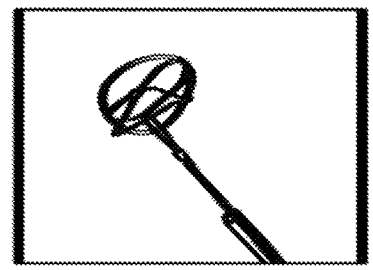
Figure 11C:
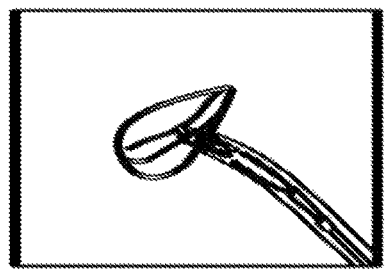
Figure 11F:
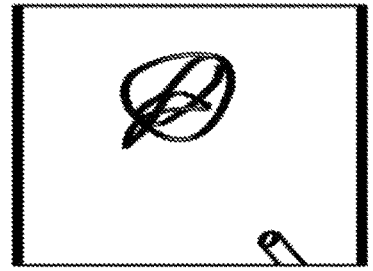
Figure 11G:
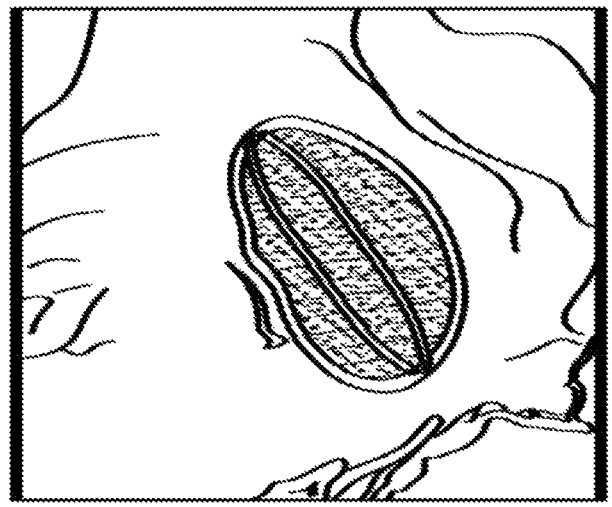
FIG. 11G is an autopsy photograph of the covered ring frame closure device of FIGS. 11A-11F implanted in the left atrium on the left side of an interatrial septum in a sheep.
Figure 11H:
FIG. 11H is an autopsy photograph of the implanted closure device depicted in FIG. 11G, illustrating deployment of a delivery bar and anchors in the right atrium on the right side of an interatrial septum.

At this point resistance and heartbeat could be felt. The tip of the flexor sheath was then gently pushed back to expand both anchors and delivery bar against the septum in the right atrial cavity (FIGS. 11C-11E). Before releasing the device, its position was assessed by contrast injection into right atrium. Upon confirmation of proper placement, the right-sided delivery bar was released from the locking catheter. Successful device implantation was achieved in both animals and no shunting of the contrast media was observed (FIG. 11F). An autopsy specimen shows the left and right sides of interatrial septum. The left atrium reveals the front part of closure device covered with SIS (FIG. 11G). The RA reveals both anchors and the delivery bar (FIG. 11H).

It is intended that the foregoing detailed description be regarded as illustrative rather than limiting, and that it be understood that it is the following claims, including all equivalents, that are intended to define the spirit and scope of this invention.

The invention claimed is:

1. A closure device comprising:
    only one circumferential frame defining a single frame plane;
    a first crossbar extending across the frame, the first crossbar having a central portion and terminal crossbar ends connectively linked to separate sites on the frame;
    a bar-shaped first anchor containing two terminal first anchor ends and a central portion attached to the central portion of the first cross bar; and
    a single sheet of biocompatible material, the sheet of biocompatible material having a periphery attached to the frame,
    wherein each of the frame, the first crossbar, and the first anchor comprises at least one flexible, substantially linear structure,
    wherein the first anchor is only indirectly connected to the frame via the first crossbar and
    wherein the first crossbar is configured to extend in an arc concave to the frame plane when deployed, and wherein the first anchor is configured to extend in an arc convex to the frame plane when deployed.

2. The device of claim 1, wherein the frame comprises one or more coils forming a closed ring.

3. The device of claim 1, wherein the substantially linear structure of each of the frame and the first crossbar comprises a hollow tube or coil, wherein one or more connecting wires extend longitudinally through the frame and the first crossbar, the one or more wires connecting the first crossbar to the frame.

4. The device of claim 1, wherein the substantially linear structure of the first anchor comprises a hollow tube or coil comprising two terminal first anchor ends, wherein an anchor wire extends longitudinally through the first anchor, the anchor wire comprising two terminally disposed grasping members frictionally engaged by the first anchor.

5. The device of claim 1, further comprising a delivery bar comprising a flexible, substantially linear structure comprising at least a tube, coil, bar or wire, the delivery bar joined between the two terminal first anchor ends.

6. The device of claim 1, further comprising:
    a second crossbar extending across the frame, the second crossbar having terminal crossbar ends connectively linked to the frame, wherein each terminal crossbar end of the second crossbar is connected to the frame at a site of connection to a terminal crossbar end of the first crossbar;
    wherein second crossbar comprises at least one flexible, substantially linear structure in the form of a tube, coil, bar, or wire, and
    wherein the second crossbar is configured to extend in an arc concave to the frame plane.

7. The device of claim 6, further comprising a second bar-shaped anchor comprising two terminal second anchor ends, the second anchor comprising a flexible, substantially linear structure, the second anchor configured to extend in an arc convex to the frame plane when deployed, wherein a central portion of the second anchor is connected to a central portion of the second crossbar.

8. The device of claim 7, further comprising a first coupling member connecting the central portion of the first anchor to the central portion of the first crossbar, and a second coupling member connecting the central portion of the second anchor to the central portion of the second crossbar.

9. The device of claim 7, wherein the substantially linear structure of the first anchor comprises a first anchor coil and the substantially linear structure of the second anchor comprises a second anchor coil, wherein one or more anchor wires extend longitudinally through the first and second anchor coils, the one or more anchor wires forming terminally disposed grasping members at each anchor end, each terminally disposed grasping member being frictionally engaged by an anchor coil end.

10. The device of claim 7, further comprising a delivery bar comprising a flexible, substantially linear structure, wherein the delivery bar is joined between a first pair of terminal anchor ends on one delivery bar end and a second pair of terminal anchor ends on a second delivery bar end.

11. The device of claim 7, wherein the substantially linear structure of the delivery bar comprises a delivery bar coil, wherein one or more wires extend longitudinally through the delivery bar coil, the wires connecting the delivery bar to the first and second anchors.

12. The device of claim 1, wherein the biocompatible material is connected to at least a portion of the frame and at least a portion of the first crossbar.

13. The device of claim 1, wherein the biocompatible material comprises ECM material.

14. A closure device comprising:
only one frame, the frame defining a frame plane;
a first crossbar extending across the frame, the first crossbar having terminal crossbar ends connectively linked to separate sites on the frame;
a second crossbar extending across the frame, the second crossbar having terminal crossbar ends connectively linked to separate sites on the frame;
a first anchor containing two terminal first anchor ends;
a second anchor containing two terminal second anchor ends;
a delivery bar joined between a first pair of terminal anchor ends on one delivery bar end and a second pair of terminal anchor ends on a second delivery bar end; and
a sheet of biocompatible material attached to the frame,
wherein the first crossbar is configured to extend in an arc concave to the frame plane when deployed, and wherein the first anchor is configured to extend in an arc convex to the frame plane when deployed, wherein each of the delivery bar, the first anchor, the second anchor, the first crossbar, and the second crossbar comprises a coil and terminally disposed wire loops;
wherein one or more wires interconnect the terminally disposed wire loops of the delivery bar with terminally disposed wire loops of the first and second anchors, and wherein one or more wires interconnect the terminally disposed wire loops of the first and second crossbars with the frame.

15. The device of claim 14, further comprising a first coupling member connecting the central portion of the first anchor to the central portion of the first crossbar, and a second coupling member connecting a central portion of the second anchor to a central portion of the second crossbar.

16. A closure device comprising:
only one circumferential frame;
a first crossbar extending across the frame, the crossbar having terminal crossbar ends connectively linked to separate sites on the frame;
a bar-shaped first anchor containing two terminal anchor ends, wherein a central portion of the first anchor is connected to a central portion of the first crossbar;
a delivery bar connecting the two terminal anchor ends; and
a single sheet of biocompatible material having a periphery attached to the frame,
wherein each of the frame, the first crossbar, the first anchor, and the delivery bar comprises at least one flexible, substantially linear structure in the form of a tube, coil, bar, or wire.

17. The device of claim 16, further comprising a second crossbar and a second anchor, the second anchor comprising two terminal second anchor ends,
wherein the second crossbar extends across the frame, the second crossbar having terminal crossbar ends connectively linked to the frame, wherein each terminal crossbar end of the second crossbar is connected to the frame at a site of connection to a terminal crossbar end of the first crossbar;
wherein a central portion of the second anchor is connected to a central portion of the second crossbar; and
wherein each of the second crossbar and the second anchor comprises at least one flexible, substantially linear structure in the form of a tube, coil, bar, or wire.

* * * * *